United States Patent
Yoshii et al.

(10) Patent No.: US 9,334,211 B2
(45) Date of Patent: May 10, 2016

(54) HYDROCRACKING CATALYST, METHOD FOR PRODUCING SAME, AND METHOD FOR PRODUCING HYDROXY COMPOUND USING SAID CATALYST

(75) Inventors: Kiyotaka Yoshii, Ube (JP); Atsushi Yamada, Ube (JP)

(73) Assignee: UBE INDUSTRIES, LTD., Yamaguchi (JP)

( * ) Notice: Subject to any disclaimer, the term of this patent is extended or adjusted under 35 U.S.C. 154(b) by 0 days.

(21) Appl. No.: 14/239,863

(22) PCT Filed: Aug. 22, 2012

(86) PCT No.: PCT/JP2012/071201
§ 371 (c)(1),
(2), (4) Date: Apr. 9, 2014

(87) PCT Pub. No.: WO2013/027766
PCT Pub. Date: Feb. 28, 2013

(65) Prior Publication Data
US 2014/0288335 A1    Sep. 25, 2014

(30) Foreign Application Priority Data

Aug. 23, 2011  (JP) ................................. 2011-182026
Mar. 13, 2012  (JP) ................................. 2012-055221
Jun. 1, 2012   (JP) ................................. 2012-126304
Jun. 15, 2012  (JP) ................................. 2012-136193

(51) Int. Cl.
| | | |
|---|---|---|
| C07C 29/10 | (2006.01) | |
| C10G 47/10 | (2006.01) | |
| C10G 47/04 | (2006.01) | |
| C07C 29/132 | (2006.01) | |
| B01J 37/10 | (2006.01) | |
| B01J 23/46 | (2006.01) | |
| B01J 23/652 | (2006.01) | |
| B01J 23/89 | (2006.01) | |
| B01J 23/68 | (2006.01) | |
| B01J 23/656 | (2006.01) | |

(52) U.S. Cl.
CPC ............. *C07C 29/103* (2013.01); *B01J 23/464* (2013.01); *B01J 23/468* (2013.01); *B01J 23/6525* (2013.01); *B01J 23/6527* (2013.01); *B01J 23/6567* (2013.01); *B01J 23/688* (2013.01); *B01J 23/8986* (2013.01); *B01J 37/10* (2013.01); *C07C 29/132* (2013.01); *C10G 47/04* (2013.01); *C10G 47/10* (2013.01)

(58) Field of Classification Search
None
See application file for complete search history.

(56) References Cited

U.S. PATENT DOCUMENTS 5,384,297 A * 1/1995 Prada et al. .................... 502/66
6,149,799 A   11/2000 Raybaud et al.
6,376,414 B1  4/2002 Antons et al.

FOREIGN PATENT DOCUMENTS

| JP | A-10-211432   | 8/1998 |
| JP | A-2002-501817 | 1/2002 |
| JP | A-2003-183200 | 7/2003 |
| JP | A-2004-526568 | 9/2004 |
| JP | A-2009-46417  | 3/2009 |

OTHER PUBLICATIONS

Database CAPLUS in STN, Acc. No. 2010:923621, Li et al., CN 101781168 A (Jul. 21, 2010) (abstract).*
Database CAPLUS in STN, Acc. No. 1986:152148, Rosenthal et al., CS 224438 B1 (Jan. 16, 1984) (abstract).*
Kaufman et al., "1,5-Pentanediol", *Organic Syntheses, Coll.*, 1955, vol. 3, p. 693.
International Search Report issued in International Application No. PCT/JP2012/071201 mailed Oct. 23, 2012.
International Preliminary Report on Patentability issued in International Application No. PCT/JP2012/071201 mailed Feb. 25, 2014.

* cited by examiner

*Primary Examiner* — Brian J Davis
(74) *Attorney, Agent, or Firm* — Oliff PLC

(57) ABSTRACT

The present invention provides a hydrocracking catalyst obtainable by mixing a metal compound (A) including any one metal of Groups 3 to 11 of the Periodic Table, a compound (B) including at least one compound selected from the group consisting of a ruthenium oxide compound (B1) and a highvalence compound (B2) including any metal of Groups 8 to 11 of the Periodic Table, and a metal oxide (C) including a metal of Group 5, Group 6 or Group 7 of the Periodic Table, and conducting reduction treatment.

4 Claims, No Drawings

HYDROCRACKING CATALYST, METHOD FOR PRODUCING SAME, AND METHOD FOR PRODUCING HYDROXY COMPOUND USING SAID CATALYST

TECHNICAL FIELD

The present invention relates to a hydrocracking catalyst and to a method for producing it. The invention further relates to a method of hydrocracking ether compounds with hydroxymethyl groups using the hydrocracking catalyst, to produce hydroxy compounds corresponding to the ether compounds.

When the ether compounds are cyclic ethers, the hydroxy compounds produced by the hydrocracking catalyst of the invention can produce the corresponding diol compounds. The obtained diol compounds are compounds that are useful as, for example, polymer starting materials for polyesters, polycarbonates and polyurethanes, resin additives, pharmaceutical and agricultural intermediate starting materials, and various solvents.

BACKGROUND ART

Conventionally known hydrocracking catalysts that can produce corresponding hydroxy compounds by hydrocracking of ether compounds with hydroxymethyl groups include, for example, catalysts comprising rhodium and at least one metal selected from the group consisting of rhenium, molybdenum and tungsten (see PTL 1, for example), catalysts having platinum or ruthenium supported on a support such as alumina and the like (see PTL 2, for example), and copper-chromium catalysts (see PTL 2, for example).

CITATION LIST

Patent Literature

[PTL 1] Japanese Unexamined Patent Application Publication No. 2009-046417
[PTL 2] Japanese Unexamined Patent Application Publication No. 2003-183200

Non-Patent Literature

[NPL 1] Organic Syntheses Col. Vol. 3, p. 693(1955)

SUMMARY OF INVENTION

Technical Problem

With all of the aforementioned proposed catalysts, however, the reaction rate, yield and selectivity have been less than satisfactory for industrial production. Another problem is that this requires the use of catalysts having severe reaction conditions and toxicity. It has therefore been desired to provide a hydrocracking catalyst that solves such problems and is industrially suitable, as well as a method for producing hydroxy compounds using the catalyst.

Therefore, according to a first aspect of the invention, there is provided a hydrocracking catalyst that solves the aforementioned problems and can produce hydroxy compounds from ether compounds with hydroxymethyl groups, at a high reaction rate, with a high yield and in a highly selective manner, and that is suitable for industrial production, and a method for producing the hydrocracking catalyst. According to a second aspect of the invention there is provided a method for producing hydroxy compounds using the hydrocracking catalyst, that allows production of hydroxy compounds at a high reaction rate, at a high yield and in a highly selective manner, and is suitable for industrial production.

Solution to Problem

The invention provides a hydrocracking catalyst obtained by mixing the following components (1), (2) and (3) and conducting reduction treatment.
(1) Metal compound (A) including any one metal of Groups 3 to 11 of the Periodic Table.
(2) Compound (B) including at least one compound selected from the group consisting of ruthenium oxide compounds (B1) and high-valence compounds (B2) including at least one metal of any of Groups 8 to 11 of the Periodic Table.
(3) Metal oxide (C) including a metal of Group 5, Group 6 or Group 7 of the Periodic Table.

Component (2) may be a ruthenium oxide compound (B1), or it may be a high-valence compound (B2) including a metal of any of Groups 8 to 11 of the Periodic Table. Component (2) may also contain both a ruthenium oxide compound (B1) and a high-valence compound (B2). Throughout the present specification, the metal compound (A), the compound (B) and the metal oxide (C) are all different compounds. Thus, the mixture of components (1), (2) and (3) contains at least three different compounds.

When the compound (B) includes a ruthenium oxide compound (B1), the ruthenium oxide compound (B1) is preferably at least one compound selected from the group consisting of ruthenium oxide and perruthenic acid salts. When the compound (B) includes a high-valence compound (B2), the high-valence compound (B2) is preferably a hydroxy metal or a hydroxy metallic acid salt.

The metal oxide (C) is preferably at least one compound selected from the group consisting of metal oxides and metallic acid peroxide salts. The reduction treatment mentioned above is preferably carried out in the presence of hydrogen.

According to the invention there is further provided a method for producing a hydrocracking catalyst comprising a step of mixing a metal compound (A) including any one metal of Groups 3 to 11 of the Periodic Table, a compound (B) including at least one compound selected from the group consisting of a ruthenium oxide compound (B1) and a high-valence compound (B2) including any metal of Groups 8 to 11 of the Periodic Table, and a metal oxide (C) including a metal of Group 5, Group 6 or Group 7 of the Periodic Table, and conducting reduction treatment to obtain a hydrocracking catalyst.

According to the invention there is still further provided a method for producing hydroxy compounds wherein an ether compound with a hydroxymethyl group is contacted with the aforementioned hydrocracking catalyst in the presence of a hydrogen source.

The ether compound is preferably a five-membered ring ether compound, six-membered ring ether compound or diallyl ether compound.

The method for producing a hydroxy compound according to the invention is preferably one in which the aforementioned ether compound represented by the following general formula (1) is contacted with the aforementioned hydrocracking catalyst in the presence of a hydrogen source, to obtain a hydroxy compound represented by the following general formula (2).

[Chemical Formula 1]

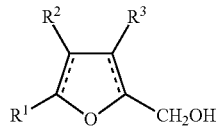
(1)

In formula (1), $R^1$, $R^2$ and $R^3$ each independently represent hydrogen or a C1-5 alkyl group, and $R^1$ and $R^2$ or $R^2$ and $R^3$ bonded to adjacent carbons may optionally be bonded together to form a ring. The bonds represented by (a) in general formula (1) represent single bonds or double bonds.

[Chemical Formula 2]

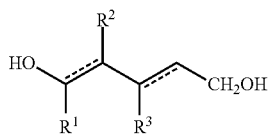
(2)

In general formula (2), $R^1$, $R^2$ and $R^3$ each independently represent hydrogen or a C1-5 alkyl group, and $R^1$ and $R^2$ or $R^2$ and $R^3$ bonded to adjacent carbons may optionally be bonded together to form a ring. A bond represented by the following formula (a) in general formula (2) also represents a single bond or a double bond.

[Chemical Formula 3]

‑ ‑ ‑ ‑ ‑ (a)

The ether compound is preferably at least one type of compound selected from the group consisting of compounds of general formulas (1a), (1b), (1c) and (1d).

[Chemical Formula 4]

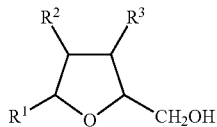
(1a)

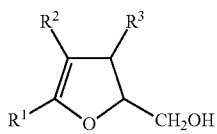
(1b)

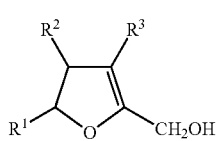
(1c)

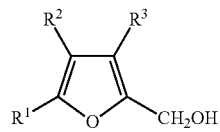
(1d)

In general formulas (1a), (1b), (1c) and (1d), $R^1$, $R^2$ and $R^3$ each independently represent hydrogen or a C1-5 alkyl group, and $R^1$ and $R^2$ or $R^2$ and $R^3$ bonded to adjacent carbons may optionally be bonded together to form a ring.

Preferably, an ether compound represented by the following general formula (3) is contacted with the aforementioned hydrocracking catalyst in the presence of a hydrogen source, to obtain a hydroxy compound represented by the following general formula (4).

[Chemical Formula 5]

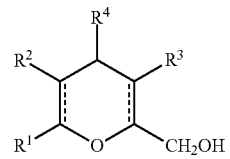
(3)

In general formula (3), $R^1$, $R^2$, $R^3$ and $R^4$ each independently represent hydrogen or a C1-5 alkyl group, and $R^1$, $R^2$, $R^3$ and $R^4$ bonded to adjacent carbons may optionally be bonded together to form a ring. A bonds represented by the following formula (a) in general formula (3) also represents single bonds or double bonds.

[Chemical Formula 6]

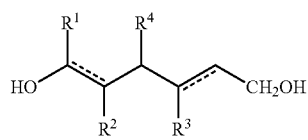
(4)

In general formula (4), $R^1$, $R^2$, $R^3$ and $R^4$ each independently represent hydrogen or a C1-5 alkyl group, and $R^1$, $R^2$, $R^3$ and $R^4$ bonded to adjacent carbons may optionally be bonded together to form a ring. A bond represented by the following formula (a) in general formula (4) also represents a single bond or a double bond.

[Chemical Formula 7]

‑ ‑ ‑ ‑ ‑ (a)

The ether compound is preferably at least one type of compound selected from the group consisting of compounds of general formulas (3a), (3b), (3c) and (3d).

[Chemical Formula 8]

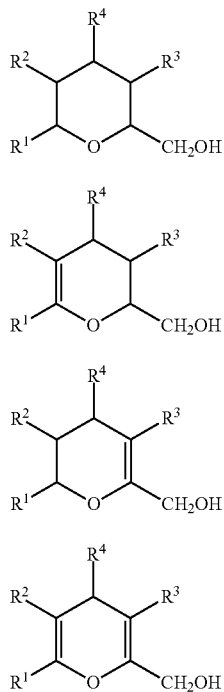

In general formulas (3a), (3b), (3c) and (3d), $R^1$, $R^2$, $R^3$ and $R^4$ each independently represent hydrogen or a C1-5 alkyl group, and $R^1$, $R^2$, $R^3$ and $R^4$ bonded to adjacent carbons may optionally be bonded together to form a ring.

Advantageous Effects of Invention

According to the invention it is possible to provide a hydrocracking catalyst capable of hydrocracking ether compounds with hydroxymethyl groups to produce hydroxy compounds corresponding to those ether compounds at a high reaction rate, at a high yield and in a highly selective manner, and also a method for producing the hydrocracking catalyst. Also according to the invention, there is provided a method for producing hydroxy compounds using the hydrocracking catalyst, that allows production of hydroxy compounds at a high reaction rate, at a high yield and in a highly selective manner, and that is suitable for industrial production.

DESCRIPTION OF EMBODIMENTS

Preferred embodiments of the invention will now be explained.
(Hydrocracking Catalyst)

The hydrocracking catalyst of this embodiment is a catalyst obtained by mixing component (1), component (2) and component (3) and subjecting the mixture to reduction treatment. Such a hydrocracking catalyst can be obtained, for example, by mixing component (1), component (2) and component (3) and then subjecting the resultant mixture to reduction treatment.
(1) Metal compound (A) including any metal of Groups 3 to 11 of the Periodic Table.
(2) Compound (B) including at least one compound selected from the group consisting of ruthenium oxide compounds (B1) and high-valence compounds (B2) including any metal of Groups 8 to 11 of the Periodic Table.
(3) Metal oxide (C) including a metal of Group 5, Group 6 or Group 7 of the Periodic Table.
(1) Metal Compound (A)

Examples of metals of Groups 3 to 11 of the Periodic Table for the metal compound (A) to be used for this embodiment include scandium, yttrium, lanthanum, cerium, neodymium, samarium, ytterbium, lutetium, titanium, zirconium, hafnium, vanadium, niobium, tantalum, chromium, molybdenum, tungsten, manganese, rhenium, iron, ruthenium, osmium, cobalt, rhodium, iridium, nickel, palladium, platinum, copper, silver and gold. Preferred among these are lanthanum, ytterbium, zirconium, hafnium, niobium, tantalum, molybdenum, tungsten, rhenium, ruthenium, cobalt, rhodium, iridium, palladium, platinum, copper and gold, with ruthenium, rhodium, iridium, platinum being more preferred. In other words, the metal compound (A) is a compound having as a constituent element a metal element belonging to any of Groups 3 to 11 of the Periodic Table.

There are no particular restrictions on the form of the metal compound (A), and for example, it may be the simple metal, a metal alloy, a metal salt, a metal complex or a metal oxide, or even a hydrate or organic compound addition product. The metal compound (A) may also be supported on a support. Metal compound (A) may be of a single type, or a mixture of two or more types may be used.

Specific examples for the metal compound (A) include lanthanum compounds such as lanthanum trichloride, lanthanum tribromide, lanthanum triiodide, lanthanum trinitrate, lanthanum phosphate, dilanthanum trisulfate and dilanthanum tricarbonate; ytterbium compounds such as ytterbium trichloride, ytterbium tribromide, ytterbium trinitrate and diytterbium trisulfate; zirconium compounds such as zirconium tetrachloride, zirconium tetrabromide, zirconium tetraiodide, zirconium tetranitrate and zirconium disulfate; hafnium compounds such as hafnium tetrachloride, hafnium tetrabromide, hafnium tetraiodide, hafnium tetranitrate and hafnium disulfate; niobium compounds such as niobium pentachloride, niobium pentabromide and niobium pentaiodide; tantalum compounds such as tantalum pentachloride, tantalum pentabromide and tantalum pentaiodide; molybdenum compounds such as molybdenum trichloride, molybdenum pentachloride and molybdenum tribromide; tungsten compounds such as tungsten tetrachloride, tungsten hexachloride and tungsten pentabromide; rhenium compounds such as rhenium trichloride, rhenium pentachloride and rhenium triiodide; ruthenium compounds such as ruthenium compounds such as rhenium compound, ruthenium trichloride, ruthenium tribromide, diammonium ruthenium pentachloride, triammonium ruthenium hexachloride, dipotassium ruthenium hexachloride, disodium ruthenium hexachloride, tripotassium ruthenium hexabromide and dipotassium ruthenium hexabromide; cobalt compounds such as cobalt dichloride, cobalt dibromide, cobalt diiodide, cobalt difluoride, cobalt dinitrate, cobalt oxide, cobalt phosphate and cobalt diacetate; rhodium compounds such as rhodium trichloride, triammonium rhodium hexachloride, tripotassium rhodium hexachloride, trisodium rhodium hexachloride and rhodium trinitrate; iridium compounds such as iridium trichloride, iridium tribromide, iridium tetrachloride, iridium tetrabromide, ammonium iridate, hexaamineiridium trichloride, pentaaminechloroiridium dichloride, triammonium iridium hexachloride, tripotassium iridium hexachloride, trisodium iridium hexachloride, diammonium iridium tetrachloride, diammonium iridium hexachloride, dipotassium iridium hexachloride, iridium hexachloride and disodium iridium hexachloride; nickel compounds such as nickel dichloride, nickel dibromide and nickel diiodide; palladium compounds such as palladium dichloride, palladium dibromide, palladium diiodide, palladium diacetate, palladium dinitrate, palladium sulfate and palladium oxide; platinum compounds such as platinum dichloride, platinum tetrachloride, platinic hexachloride, platinum dibromide, platinum tetrabromide, platinic hexabromide, platinum diiodide, platinum tetraiodide, diammonium platinum dichloride, diammonium platinum hexachloride, diammonium platinum hexachloride, diammonium platinum tetrachloride, disodium platinum hexachloride, dipotassium platinum tetrachloride, dipotassium platinum hexachloride, diammonium platinum dibromide, dipotassium platinum tetrabromide, diammonium platinum hexabromide, sodium platinum hexaiodide, potassium platinum hexaiodide, platinum oxide and hexahydroxoplatinic acid; copper compounds such as copper monochloride, copper dichloride and diammonium copper dichloride; silver compounds such as silver monochloride, silver monobromide and silver monoiodide; and gold compounds such as gold monochloride, gold trichloride, auric tetrachloride, gold tribromide and gold triiodide. Among these there are preferably used ruthenium trichloride, cobalt dichloride, rhodium trichloride, iridium trichloride, iridium tetrachloride, iridic hexachloride, nickel dichloride, palladium dichloride, platinum dichloride, copper dichloride and auric tetrachloride.

(2) Compound (B)

According to this embodiment, the compound (B) is a compound (B) including a ruthenium oxide compound (B1) and a high-valence compound (B2) including any metal of Groups 8 to 11 of the Periodic Table.

[Ruthenium Oxide Compound (B1)]

The ruthenium oxide compound (B1) used for this embodiment is preferably at least one type of compound selected from the group consisting of ruthenium oxides and perruthenic acid salts. Examples of ruthenium oxides include ruthenium dioxide, ruthenium trioxide and ruthenium tetraoxide. Ruthenium tetraoxide is preferably used, among these. Examples of perruthenic acid salts include potassium perruthenate, tetrapropylammonium perruthenate, tetrabutylammonium perruthenate, dipotassium tetraoxoruthenate(VI) and disodium tetraoxoruthenate(VI). Preferred for use among these are potassium perruthenate, tetrapropylammonium perruthenate, dipotassium tetraoxoruthenate(VI) and disodium tetraoxoruthenate(VI). These ruthenium oxide compounds (B1) may be hydrates, water-soluble solutions or organic compound addition products, or they may be supported on a support.

[High-valence Metal Compound (B2)]

Examples for the metal of any of Groups 8 to 11 of the Periodic Table in the high-valence metal compound (B2) to be used for this embodiment include iron, ruthenium, osmium, cobalt, rhodium, iridium, nickel, palladium, platinum, copper, silver and gold. Preferred among these are ruthenium, rhodium, iridium, palladium, platinum and gold. In other words, the high-valence metal compound (B2) is a compound having as a constituent element a metal element belonging to any of Groups 8 to 11 of the Periodic Table. The high-valence metal compound (B2) having ruthenium as the metal of any of Groups 8 to 11 of the Periodic Table will sometimes be a ruthenium oxide compound (B1). That is, when the ruthenium oxide compound (B1) is a compound having high-valence ruthenium as a constituent element, that compound will also qualify as a high-valence metal compound (B2). Even when such a compound has been used, it will of course still fall under the definition of a hydrocracking catalyst according to this embodiment.

The term "high-valence metal" as used in the present specification means a metal having a metal valence of 3 or greater. The form of the high-valence metal compound (B2) is not particularly restricted, and for example, it may be a hydrate or an organic compound addition product. Alternatively, it may be supported on a support. The high-valence metal compound (B2) may be of a single type, or a mixture of two or more types may be used.

The high-valence metal compound (B2) used is preferably at least one compound selected from the group consisting of hydroxy metals and hydroxy metallic acid salts. Specific examples include trihydroxyiron(III), tetrahydroxyruthenium(IV), tetrahydroxyosmium(IV), trihydroxycobalt(III), trisodium hexahydroxyrhodate(III), tripotassium hexahydroxyrhodate(III), disodium hexahydroxyrhodate(IV), dipotassium hexahydroxyrhodate(IV), disodium hexahydroxyiridate(IV), dipotassium hexahydroxyiridate(IV), disodium hexahydroxypalladate(IV), dipotassium hexahydroxypalladate(IV), hexahydroxyplatinic(IV) acid, disodium hexahydroxyplatinate(IV), dipotassium hexahydroxyplatinate(IV) and trihydroxy gold(III). It is preferred to use tetrahydroxyruthenium(IV), trisodium hexahydroxyrhodate(III), tripotassium hexahydroxyrhodate(III), disodium hexahydroxyrhodate(IV), dipotassium hexahydroxyrhodate(IV), disodium hexahydroxyiridate(IV), dipotassium hexahydroxyiridate(IV), disodium hexahydroxypalladate(IV), dipotassium hexahydroxypalladate(IV), hexahydroxyplatinic(IV) acid, disodium hexahydroxyplatinate(IV), dipotassium hexahydroxyplatinate(IV) or trihydroxy gold(III), and more preferably trisodium hexahydroxyrhodate (III), dipotassium hexahydroxyiridate(IV), dipotassium hexahydroxypalladate (IV), hexahydroxyplatinic(IV) acid, disodium hexahydroxyplatinate(IV) or trihydroxy gold(III). These high-valence metal compounds (B2) may be used as hydrates or organic compound addition products, or they may be supported on supports.

The compound (B) is a different compound from the metal compound (A). Specifically, in order to obtain a hydrocracking catalyst according to this embodiment, the compound (B) used is a different compound from the metal compound (A). However, the metal compound (A) and metal compound (B) may contain the same metals.

(3) Metal Oxide (C)

Examples of metals for the metal oxide (C) containing a metal of Group 5, Group 6 or Group 7 of the Periodic Table, to be used for this embodiment, include vanadium, niobium, tantalum, chromium, molybdenum, tungsten, manganese, technetium and rhenium. Preferred metals are vanadium, molybdenum, tungsten and rhenium. In other words, metal compound (C) is a compound having as a constituent element a metal element belonging to Group 5, Group 6 or Group 7 of the Periodic Table.

The form of the metal oxide (C) is not particularly restricted so long as it is a compound with one metal-oxygen bond, and it may be a hydrate or organic compound addition product, for example. The metal oxide (C) may also be supported on a support. The metal oxide may be of a single type, or a mixture of two or more types may be used.

The metal oxide (C) used is preferably at least one compound selected from the group consisting of metal oxides and metallic acid peroxide salts. Specific examples include vanadium oxides such as vanadium oxide, divanadium trioxide, vanadium dioxide, divanadium pentaoxide, vanadium tribromide, potassium pyrovanadate, potassium tetraoxovanadate (V), potassium trioxovanadate(V), sodium trioxovanadate (V), sodium pyrovanadate and lithium trioxovanadate(V); molybdenum oxides such as silicomolybdic acid, ammonium tetracosaoxoheptamolybdate (VI), potassium tetraoxomolybdate(VI), tetraoxocalcium molybdate, sodium tetraoxomolybdate(VI), magnesium tetraoxomolybdate(VI), lithium tetraoxomolybdate(VI), molybdenum dioxide and molybdenum trioxide; tungsten oxides such as sodium tetraoxotungstate(VI), cadmium(II) tetraoxotungstate(VI), potassium tetraoxotungstate and calcium tetraoxotungstate(VI); and rhenium oxides such as ammonium tetraoxorhenate(VII), potassium tetraoxorhenate(VII), sodium tetraoxorhenate (VII), rhenium dioxide, rhenium trioxide and dirhenium heptaoxide. Preferred for use are divanadium pentaoxide, potassium trioxovanadate(V), sodium trioxovanadate(V), sodium pyrovanadate, sodium tetraoxotungstate(VI), silicomolybdic acid, ammonium tetracosaoxoheptamolybdate(VI), sodium tetraoxomolybdate(VI), ammonium tetraoxorhenate(VII), potassium tetraoxorhenate(VII) and dirhenium heptaoxide.

Specific examples for the metal oxide (C) are the same as for the metal compound (A). In order to obtain a hydrocracking catalyst for this embodiment, however, the component used for the metal oxide (C) is different from the metal compound (A). The metal compound (A) and the metal oxide (C) may contain the same metals. That is, the hydrocracking catalyst of this embodiment is produced using at least three different compounds, which may have the same metal elements as constituent elements.

The hydrocracking catalyst of this embodiment can be obtained by a production method having a first step in which the starting materials are mixed to obtain a mixture, and a second step in which the mixture is subjected to reduction treatment. In the first step, the metal compound (A), the compound (B) and the metal oxide (C) are mixed. There are no particular restrictions on the mixing order, but the preferred method is mixing the metal compound (A) and the compound (B) first and then adding the metal oxide (C). As the compound (B) there may be used a ruthenium oxide compound (B1) and/or high-valence metal compound (B2).

As a more specific production method, a solvent solution (for example, a water-soluble solution) is obtained by adding the metal compound (A) and the compound (B) to a solvent (for example, water) in the first step. The obtained water-soluble solution is heated and stirred at preferably 60° C. to 200° C. and more preferably 100° C. to 150° C. Next, the metal oxide (C) is added to the water-soluble solution and the mixture is heated and stirred at preferably 60° C. to 200° C. and more preferably 100° C. to 150° C. to obtain a mixture.

The amount of the compound (B) used for mixing is preferably 0.1 to 30 mol and more preferably 0.2 to 20 mol with respect to 1 mol of the metal compound (A). The amount of the metal oxide (C) used is preferably 0.5 to 30 mol and more preferably 1 to 20 mol with respect to 1 mol of the metal compound (A). These values are the values for the metal compound (A) and the metal oxide (C) each in terms of the metal atom.

The mixture obtained in the first step may be directly subjected to reduction treatment in the second step to produce a hydrocracking catalyst. The reduction treatment can be carried out using a common reducing agent that is able to generate hydrogen. For example, a method of contacting the mixture with hydrogen gas may be suitably employed. The contact temperature during contact between the mixture and the hydrogen gas is preferably 40° C. to 300° C. and more preferably 50° C. to 200° C., and the contact pressure is preferably from normal pressure to 20 MPa and more preferably 0.2 to 15 MPa. The first step and second step may also be carried out simultaneously. Specifically, reduction treatment may be conducted while preparing the mixture, to produce the hydrocracking catalyst.

The hydrocracking catalyst obtained by the reduction treatment may be first filtered and rinsed for isolation, or it may be used directly in suspension form to produce a hydroxy compound.

The catalyst for hydrogenation reaction may be a catalyst supported on a support (supported catalyst). Such a supported catalyst can be produced by adding the support during preparation of the mixture. The support used is suitably a porous support. Specific examples include silica, alumina, silica-alumina (aluminosilicate), ceria, magnesia, calcia, titania, silica-titania (titanosilicate), zirconia and active carbon, zeolite, and mesoporous materials (mesoporous alumina, mesoporous silica, mesoporous carbon). These supports may be used alone or in combinations of two or more different types.

When the hydrocracking catalyst is a supported catalyst, the second step may be followed by a third step in which a composition comprising the catalyst and the support is fired. The firing temperature is preferably 50° C. to 800° C. and more preferably 100° C. to 600° C. The firing time may be appropriately adjusted, and is preferably 0.1 to 20 hours and more preferably 0.25 to 15 hours.

The hydrocracking catalyst obtained by this method can be used as a catalyst to produce a hydroxy compound from an ether compound with a hydroxymethyl group. A preferred embodiment of the method for producing a hydroxy compound using the aforementioned hydrocracking catalyst will now be described.

(Production of Hydroxy Compound)

By contacting the hydrocracking catalyst with an ether compound having a hydroxymethyl group, in the presence of a hydrogen source, it is possible to produce a hydroxy compound. The ether compound may be a cyclic or linear ether compound, and is preferably a five-membered ring ether compound, six-membered ring ether compound or dialkyl ether compound.

(Production Method Using Five-membered Ring Ether Compound with Hydroxymethyl Group)

When the ether compound is a five-membered ring ether compound, the hydrocracking catalyst is contacted with an ether compound having a hydroxymethyl group represented by general formula (1), in the presence of a hydrogen source.

[Chemical Formula 9]

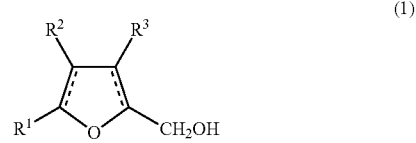

(1)

In general formula (1), $R^1$, $R^2$ and $R^3$ each independently represent hydrogen or a C1-5 alkyl group. $R^1$ and $R^2$, $R^2$ and $R^3$ bonded to adjacent carbons may optionally be bonded together to form a ring. A bond represented by the following formula (a) in general formula (1) represents a single bond or a double bond.

[Chemical Formula 10]

───── (a)

When the ether compound of general formula (1) is contacted with the hydrocracking catalyst, a hydroxy compound represented by general formula (2) is produced. The hydroxy compound represented by general formula (2) is 1,5-diol compound.

[Chemical Formula 11]

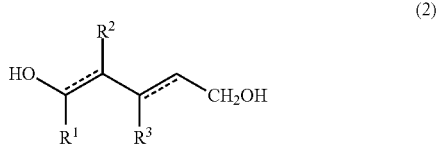
(2)

In general formula (2), $R^1$, $R^2$ and $R^3$ each independently represent hydrogen or a C1-5 alkyl group. $R^1$ and $R^2$, $R^2$ and $R^3$ bonded to adjacent carbons may optionally be bonded together to form a ring. A bond represented by the following formula (a) in general formula (2) represents a single bond or a double bond.

[Chemical Formula 12]

(a)

In general formula (1), $R^1$, $R^2$ and $R^3$ each independently represent hydrogen or a C1-5 alkyl group, with specific examples including hydrogen and methyl, ethyl, propyl, butyl and pentyl groups. These groups includes various isomers. Also, $R^1$ and $R^2$, and $R^2$ and $R^3$, which are bonded to adjacent carbons, may be bonded together to form rings (for example, cyclohexane rings).

Ether compounds with hydroxymethyl groups represented by general formula (1) include, specifically, compounds represented by general formulas (1a) to (1d).

[Chemical Formula 13]

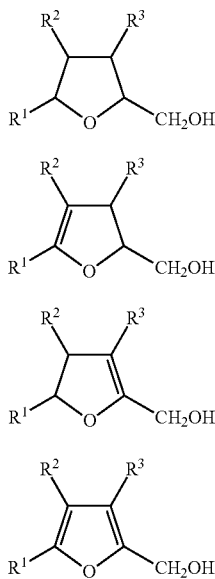
(1a)
(1b)
(1c)
(1d)

In general formulas (1a) to (1d), $R^1$, $R^2$ and $R^3$ have the same definitions as in general formula (1).

Specific examples of five-membered ring ether compounds with hydroxymethyl groups represented by general formula (1) include tetrahydrofurfuryl alcohol, 2,3-dihydrofurfuryl alcohol, 4,5-dihydrofurfuryl alcohol, furfuryl alcohol, 5-methyltetrahydrofurfuryl alcohol, 5-ethyltetrahydrofurfuryl alcohol, 5-propyltetrahydrofurfuryl alcohol, 5-butyltetrahydrofurfuryl alcohol and 5-pentyltetrahydrofurfuryl alcohol. Preferred for use are furfuryl alcohol, 4,5-dihydrofurfuryl alcohol, tetrahydrofurfuryl alcohol and 5-methyltetrahydrofurfuryl alcohol, with tetrahydrofurfuryl alcohol being more preferred.

The hydroxy compound obtained by contacting the hydrocracking catalyst with the ether compound having a hydroxymethyl group represented by general formula (1) is represented by general formula (2) above (i.e. a 1,5-diol compound).

Specific examples of hydroxy compounds represented by general formulas (1a) to (1d) include 1,5-pentanediol, 1-pentene-1,5-diol, 2-pentene-1,5-diol, penta-1,3-diene-1,5-diol, 1,5-hexanediol, 1,5-heptanediol, 1,5-octanediol, 1,5-nonanediol and 1,5-decanediol. Preferably used are 1,5-pentanediol, 1-pentene-1,5-diol, 2-pentene-1,5-diol and 1,5-hexanediol, with 1,5-pentanediol being more preferred.

(Production Method Using Six-membered Ring Ether Compound with Hydroxymethyl Group)

When the ether compound is a six-membered ring ether compound, the hydrocracking catalyst is contacted with an ether compound having a hydroxymethyl group represented by general formula (3), in the presence of a hydrogen source.

[Chemical Formula 14]

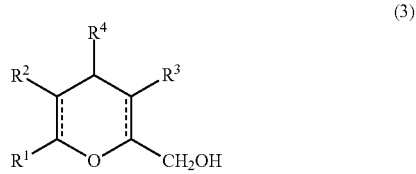
(3)

In general formula (3), $R^1$, $R^2$, $R^3$ and $R^4$ each independently represent hydrogen or C1-5 alkyl. $R^1$ and $R^2$, $R^2$ and $R^4$ or $R^3$ and $R^4$, which are bonded to adjacent carbons, may be bonded together to form a ring. A bond represented by the following formula (a) in general formula (3) represents a single bond or a double bond.

[Chemical Formula 15]

(a)

When the ether compound of general formula (3) is contacted with the hydrocracking catalyst in the presence of a hydrogen source, a hydroxy compound represented by general formula (4) is produced. The hydroxy compound represented by general formula (4) is a 1,6-diol compound.

[Chemical Formula 16]

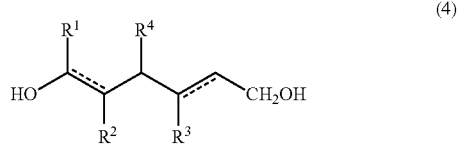
(4)

[In general formula (4), $R^1$, $R^2$, $R^3$ and $R^4$ each independently represent hydrogen or C1-5 alkyl. $R^1$ and $R^2$, $R^2$ and $R^4$ or $R^3$ and $R^4$, which are bonded to adjacent carbons, may be bonded together to form a ring. A bond represented by the following formula (a) in general formula (4) represents a single bond or a double bond.

[Chemical Formula 17]

(a)

In general formula (3), $R^1$, $R^2$, $R^3$ and $R^4$ each independently represent hydrogen or a C1-5 alkyl group, with specific examples including hydrogen and methyl, ethyl, propyl, butyl and pentyl groups. These groups include various isomers. Also, $R^1$, $R^2$, $R^3$ and $R^4$, which are bonded to adjacent carbons, may each be bonded together to form rings (for example, cyclohexane rings).

Six-membered ring ether compounds with hydroxymethyl groups represented by general formula (3) include, specifically, compounds represented by general formulas (3a) to (3d).

[Chemical Formula 18]

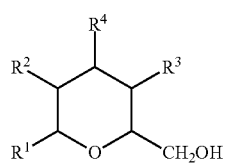

(3a)

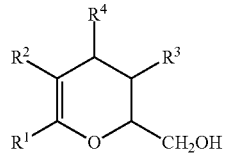

(3b)

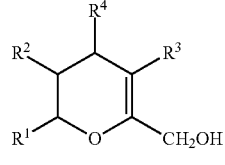

(3c)

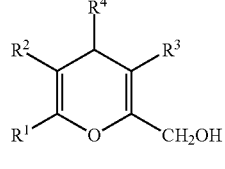

(3d)

In general formulas (3a) to (3d), $R^1$, $R^2$, $R^3$ and $R^4$ each independently represent hydrogen or C1-5 alkyl. $R^1$ and $R^2$, $R^2$ and $R^4$ or $R^3$ and $R^4$, which are bonded to adjacent carbons, may each be bonded together to form a ring.

Examples of six-membered ring ether compounds with hydroxymethyl groups represented by general formulas (3a) to (3d) include tetrahydropyran-2-methanol, 3,4-dihydro-2H-pyran-2-methanol, 3,4-dihydro-2H-pyran-6-methanol, 4H-pyran-2-methanol, 6-methyltetrahydropyran-2-methanol, 6-ethyltetrahydropyran-2-methanol, 6-propyltetrahydropyran-2-methanol, 6-butyltetrahydropyran-2-methanol and 6-pentyltetrahydropyran-2-methanol. Preferred for use are tetrahydropyran-2-methanol, 3,4-dihydro-2H-pyran-2-methanol, 3,4-dihydro-2H-pyran-6-methanol, 4H-pyran-2-methanol, 6-methyltetrahydropyran-2-methanol and 6-ethyltetrahydropyran-2-methanol, with tetrahydropyran-2-methanol being more preferred.

The hydroxy compound obtained by contacting the hydrocracking catalyst with the ether compound having a hydroxymethyl group represented by general formula (3) is represented by general formula (4) above (i.e. a 1,6-diol compound).

Examples of hydroxy compounds represented by general formula (4) include 1,6-hexanediol, 1-hexene-1,6-diol, 2-hexene-1,6-diol, hexa-1,4-diene-1,6-diol, 1,6-heptanediol, 1,6-octanediol, 1,6-nonanediol, 1,6-decanediol and 1,6-undecanediol. Preferred for use among these are 1,6-hexanediol, 1-hexene-1,6-diol, 2-hexene-1,6-diol, hexa-1,4-diene-1,6-diol, 1,6-heptanediol and 1,6-octanediol, with 1,6-hexanediol being more preferred.

(Production Method Using Dialkyl Ether Compound with Hydroxymethyl Group)

On the other hand, when the ether compound is a dialkyl ether compound, the hydrocracking catalyst is contacted with an ether compound having a hydroxymethyl group represented by general formula (5), in the presence of a hydrogen source.

[Chemical Formula 19]

(5)

In general formula (5), $R^1$, $R^2$ and $R^3$ each independently represent hydrogen or a C1-5 alkyl group, with examples including hydrogen and methyl, ethyl, propyl, butyl and pentyl groups. These groups include various isomers. $R^1$ and $R^2$ may also be bonded together to form a ring.

Contacting a hydrocracking catalyst with an ether compound having a hydroxymethyl group represented by general formula (5) yields a hydroxy compound represented by general formula (6a) or (6b). The hydroxy compounds represented by general formula (6a) and (6b) are monool compounds.

[Chemical Formula 20]

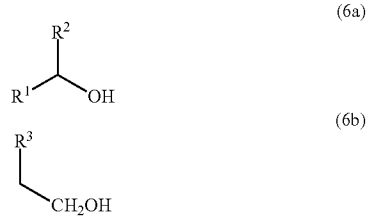

(6a)

(6b)

In general formulas (6a) and (6b), $R^1$, $R^2$ and $R^3$ each independently represent hydrogen or a C1-5 alkyl group, with examples including hydrogen and methyl, ethyl, propyl, butyl and pentyl groups. These groups include various isomers. $R^1$ and $R^2$ may also be bonded together to form a ring.

Specific examples of dialkyl ether compounds having hydroxymethyl groups represented by general formula (5) include 2-methoxyethanol, 2-ethoxyethanol, 2-n-propoxyethanol, 2-isopropoxyethanol, 2-n-butoxyethanol, 2-isobutoxyethanol, 2-t-butoxyethanol, 2-n-pentoxyethanol, 2-cyclopropoxyethanol, 2-cyclobutoxyethanol, 2-cyclopentoxyethanol, 2-cyclohexyloxyethanol, 2-methoxypropanol, 2-ethoxypropanol, 2-n-propoxypropanol, 2-isopropoxypropanol, 2-n-butoxypropanol, 2-isobutoxypropanol, 2-t-butoxypropanol, 2-n-pentoxypropanol, 2-cyclopropoxypropanol, 2-cyclobutoxypropanol, 2-cyclopentoxypropanol, 2-cyclohexyloxypropanol, 2-methoxybutanol, 2-ethoxybutanol, 2-n-propoxybutanol, 2-isopropoxybutanol, 2-n-butoxybutanol, 2-isobutoxybutanol, 2-t-butoxybutanol, 2-n-pentoxybutanol, 2-cyclopropoxybutanol, 2-cyclobutoxybutanol, 2-cyclopentoxybutanol, 2-cyclohexyloxybutanol, 2-methoxypentanol, 2-ethoxypentanol, 2-n-propoxypentanol, 2-isopropoxypentanol, 2-n-butoxypentanol, 2-isobutoxypentanol, 2-t-butoxypentanol, 2-n-pentoxypentanol, 2-cyclopropoxypentanol, 2-cyclobutoxypentanol, 2-cyclopentoxypentanol, 2-cyclohexyloxypentanol, 2-methoxyhexanol, 2-ethoxyhexanol, 2-n-propoxyhexanol, 2-isopropoxyhexanol, 2-n-butoxyhexanol, 2-isobutoxyhexanol, 2-t-butoxyhexanol, 2-n-pentoxyhexanol, 2-cyclopropoxyhexanol, 2-cyclobutoxyhexanol, 2-cyclopentoxyhexanol, 2-cyclohexyloxyhexanol, 2-methoxyheptanol, 2-ethoxyheptanol, 2-n-propoxyheptanol, 2-isopropoxyheptanol, 2-n-butoxyheptanol, 2-isobutoxyheptanol, 2-t-butoxyheptanol, 2-n-pentoxyheptanol, 2-cyclopropoxyheptanol, 2-cyclobutoxyheptanol, 2-cyclopentoxyheptanol and 2-cyclohexyloxyheptanol. Preferred for use among these are 2-methoxyethanol, 2-ethoxyethanol, 2-n-propoxyethanol, 2-isopropoxyethanol, 2-n-butoxyethanol, 2-isobutoxyethanol, 2-t-butoxyethanol, 2-n-pentoxyethanol, 2-cyclopropoxyethanol, 2-cyclobutoxyethanol, 2-cyclopentoxyethanol and 2-cyclohexyloxyethanol, with 2-methoxyethanol, 2-ethoxyethanol, 2-n-propoxyethanol, 2-n-butoxyethanol, 2-cyclopropoxyethanol and 2-cyclohexyloxyethanol being more preferred.

Specific examples of hydroxy compounds (monool compounds) represented by general formulas (6a) and (6b) include ethanol, n-propyl alcohol, isopropyl alcohol, n-butyl alcohol, n-pentanol, n-hexanol, n-heptanol, 2-butanol, 2-pentanol, 2-hexanol, 2-heptanol, 3-pentanol, 3-hexanol, 3-heptanol, 3-octanol, cyclopropanol, cyclobutanol, cyclopentanol and cyclohexanol. Preferred among these are ethanol, n-propyl alcohol, isopropyl alcohol, n-butyl alcohol, n-pentanol, n-hexanol, n-heptanol, cyclopropanol, cyclobutanol, cyclopentanol and cyclohexanol.

The reaction that proceeds during production of a hydroxy compound by contact between a hydrocracking catalyst and an ether compound having a hydroxymethyl group in the presence of a hydrogen source will also be referred to below as "the reaction of this embodiment".

The reaction of this embodiment will now be described in detail. The reaction of this embodiment is a reaction in which, in an ether compound with a hydroxymethyl group, the bond is broken between the carbon to which the hydroxymethyl group is bonded and the oxygen forming the ether group, to obtain the corresponding hydroxy compound.

[Chemical Formula 21]

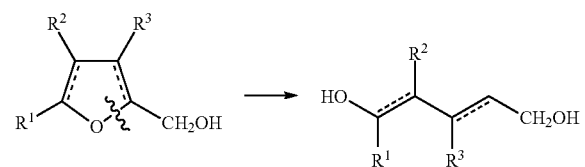

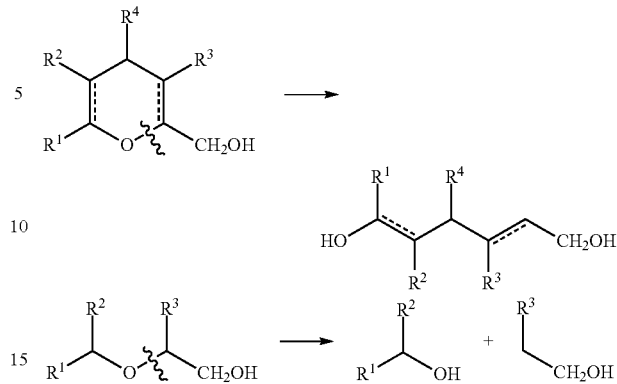

In this general formula, $R^1$, $R^2$ and $R^3$ have the same definitions as above. A bond represented by formula (a) in the general formula represents a single bond or a double bond.

[Chemical Formula 22]

$$----- \quad (a)$$

The amount of hydrocracking catalyst to be used for the reaction of this embodiment is preferably 0.0005 to 0.1 mol and more preferably 0.001 to 0.075 mol with respect to 1 mol of the ether compound with a hydroxymethyl group, in terms of the metal atom of Groups 3 to 11 of the Periodic Table in the metal compound (A). Using such an amount will allow a sufficient reaction rate to be obtained, while yielding a hydroxy compound at high yield and with high selectively. The hydrocracking catalyst used may also be a plurality of different separately prepared catalysts.

The hydrogen source to be used for the reaction of this embodiment is not particularly restricted so long as it is a compound that supplies hydrogen, and examples include reducing gases such as hydrogen gas and ammonia gas (which may be diluted with inert gases such as nitrogen, helium or argon); water; alcohols such as methanol, ethanol and isopropyl alcohol; organic acids such as formic acid, acetic acid and chloroformic acid; and inorganic acids such as hydrochloric acid and sulfuric acid. Preferred among these are reducing gases, with hydrogen gas being more preferred for use.

The amount of the hydrogen source is preferably 5 to 200 mol and more preferably 10 to 160 mol with respect to 1 mol of the ether compound with a hydroxymethyl group. Using such an amount will allow a sufficient reaction rate to be obtained, while yielding a hydroxy compound at high yield and with high selectively. The hydrocracking catalyst used may also be a plurality of different separately prepared catalysts.

The reaction of this embodiment is preferably carried out in a solvent. The solvent to be used is not particularly restricted so long as it does not inhibit the reaction, and examples include water; alcohols such as methanol, ethanol, n-propyl alcohol, isopropyl alcohol, n-butyl alcohol, t-butyl alcohol and ethylene glycol; hydrocarbons such as heptane, hexane, cyclohexane and toluene; amides such as N,N-dimethylformamide, N,N-dimethylacetamide and N-methyl-2- pyrrolidone; ethers such as diethyl ether, diisopropyl ether, 1,2-dimethoxyethane, 1,2-diethoxyethane, diethylene glycol dimethyl ether, diethylene glycol diethyl ether, tetrahydrofuran and dioxane; and halogenated hydrocarbons such as methylene chloride, dichloroethane and chlorocyclohexane. Preferred among these are water, hydrocarbons and ethers, with water, cyclohexane and 1,2-diethoxyethane being more preferred. The solvent used may be of a single type, or a mixture of two or more types may be used.

The amount of solvent used is preferably 0.05 to 100 g and more preferably 0.1 to 20 g with respect to 1 g of the ether compound with a hydroxymethyl group. Using such an amount will allow rapid stirring to be carried out and will also allow the reaction to proceed smoothly.

The form of the reaction of this embodiment may be selected from among batch-type and continuous-type methods, depending on the type of catalyst. Also, depending on the nature of the catalyst, it may be conducted in a reaction system that is either a homogeneous system or a non-homogeneous system (suspension reaction). The reaction may also be conducted continuously in a fixed bed, if the catalyst is supported on a support.

The reaction of this embodiment is carried out by a method in which, for example, an ether compound with a hydroxymethyl group is mixed with a hydrocracking catalyst and a solvent and stirred in the presence of a hydrogen source for reaction. The reaction temperature is preferably 25° C. to 200° C. and more preferably 50° C. to 150° C., and the reaction pressure is preferably from normal pressure to 20 MPa and more preferably 0.2 to 15 MPa, as the hydrogen partial pressure. By limiting the reaction temperature and reaction pressure in these ranges, it is possible to minimize generation of by-products and to obtain a hydroxy compound as the target compound at a high reaction rate, at a high yield and in a highly selective manner. In order to promote the reaction, an acid such as hydrochloric acid, sulfuric acid or phosphoric acid may be added as necessary. The amount of such an acid is preferably 0.0001 to 0.1 mol and more preferably 0.001 to 0.04 mol, with respect to 1 mol of the ether compound with a hydroxymethyl group.

Conducting the reaction of this embodiment yields a hydroxy compound as the desired product. Upon completion of the reaction, the hydroxy compound may be isolated and purified from the resulting reaction mixture by common procedures such as filtration, concentration, extraction, distillation, sublimation, recrystallization and column chromatography.

In the reaction of this embodiment, the reaction may be carried out with addition of an amine compound together with the hydrocracking catalyst. For example, there may be mentioned a method of adding an amine compound after mixing the hydrocracking catalyst with the ether compound having a hydroxymethyl group so that it is copresent during the reaction, or a method of adding and mixing an amine compound when the hydrocracking catalyst is produced. The manner in which the amine compound is added to the reaction system during the reaction may involve addition of the amine compound at any desired timing.

The amine compound is preferably one having two or more nitrogen atoms. Examples of such amine compounds include aliphatic diamines such as diaminomethane, 1,2-diaminoethane, 1,3-diaminopropane, 1,4-diaminobutane, 1,5-diaminopentane, 1,2-diaminocyclohexane, 1,3-diaminocyclohexane and 1,4-diaminocyclohexane; aromatic diamines such as 1,2-diaminobenzene, 1,3-diaminobenzene, 1,4-diaminobenzene, 2,3-diaminonaphthalene and 1,8-diaminonaphthalene; and heterocyclic amines such as 2-aminopyridine, 3-aminopyridine, 4-aminopyridine, 4-aminopiperidine, 2,3-diaminopyridine, 2,4-diaminopyridine, 2,5-diaminopyridine, 2,6-diaminopyridine, 2-aminoquinoline, 3-aminoquinoline and 4-aminoquinoline. Preferred among these are 1,2-diaminoethane, 1,3-diaminopropane, 1,4-diaminobutane, 1,5-diaminopentane, 1,2-diaminocyclohexane, 1,3-diaminocyclohexane, 1,4-diaminocyclohexane, 1,2-diaminobenzene, 1,3-diaminobenzene, 1,4-diaminobenzene, 2-aminopyridine, 3-aminopyridine and 4-aminopyridine, with 1,2-diaminoethane, 1,3-diaminopropane, 1,4-diaminobutane, 1,2-diaminocyclohexane, 1,3-diaminocyclohexane, 1,4-diaminocyclohexane and 1,2-diaminobenzene being more preferred. These amine compounds used may be of a single type, or a mixture of two or more types may be used.

The amount of the amine compound used is preferably 0.01 to 5.0 mol and more preferably 0.1 to 1.0 mol with respect to 1 mol of the metal of the compound (B). By using such an amount it is possible to avoid lowering selectivity of the desired hydroxy compound, with consecutive reaction or low molecularization decomposition that takes place during the reaction.

Preferred embodiments of the invention were described above, but the invention is not limited to these embodiments.

EXAMPLES

The present invention will now be explained in greater detail with reference to examples, with the understanding that the invention is not meant to be limited to these examples.

The following starting materials (1) to (3) were used to prepare and evaluate hydrocracking catalysts, as described below.

(1) Metal compound (A) including a metal of any of Groups 3 to 11 of the Periodic Table.
(2) Ruthenium oxide compound (B1)
(3) Metal oxide (C) including any metal of Groups 5 to 7 of the Periodic Table.

Example 1-1

Production of Hydrocracking Catalyst

As starting materials there were prepared 44.4 mg (0.12 mmol) of iridium trichloride.n hydrate (product of Ishizu Shiyaku, iridium concentration: 53 mass %) and 24.5 mg (0.12 mmol) of potassium perruthenate(VII). After adding the starting materials and 5 ml of water into an autoclave equipped with a 50 ml glass inner cylindrical tube, the mixture was heated and stirred at 120° C. for 30 minutes to prepare a solution. This was temporarily cooled to room temperature. To the cooled solution there was added 34.7 mg (0.12 mmol) of potassium tetraoxorhenate(VII), and the mixture was again heated and stirred at 120° C. for 30 minutes. It was then pressurized to 8 MPa at room temperature under a hydrogen atmosphere, and heated and stirred at 120° C. for 1 hour for reduction treatment of the mixture. The obtained solution was cooled to room temperature, the aqueous layer was removed by decantation and the hydrocracking catalyst (hereunder also referred to as "Ir—Ru—Re catalyst (1)") was obtained as a residue.

Example 1-2

Synthesis of 1,5-pentanediol

[Chemical Formula 23]

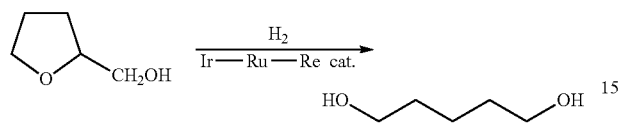

After placing the residue obtained in Example 1-1 (Ir—Ru—Re catalyst (1)) and 5.00 g (2.45 mmol) of a 5% tetrahydrofurfuryl alcohol water-soluble solution in the same apparatus as Example 1-1, the mixture was pressurized to 8 MPa with hydrogen gas and then reacted at 120° C. for 2 hours while stirring. This caused the reaction represented above to proceed. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 100%, a 1,5-pentanediol yield of 19.7% and a selectivity of 19.7%. Absolutely no 1,2-pentanediol by-product was detected.

The "5% tetrahydrofurfuryl alcohol water-soluble solution" was a water-soluble solution containing 5 mass % tetrahydrofurfuryl alcohol, based on the total water-soluble solution. The conversion rates in the examples and comparative examples are the molar ratios of starting materials remaining in the filtrates, with respect to the starting materials used (tetrahydrofurfuryl alcohol in Example 1-2). The yields are the molar ratios of products (1,5-pentanediol in Example 1-2) with respect to the starting materials used. The selectivities are the molar ratios of products with respect to the starting materials consumed.

Example 1-3

Synthesis of 1,5-pentanediol

Reaction was carried out in the same manner as Example 1-2, except that the reaction temperature in Example 1-2 was changed from 120° C. to 80° C. As a result, the tetrahydrofurfuryl alcohol conversion rate was 88.0%, the 1,5-pentanediol yield was 69.3% and the selectivity was 78.7%. Absolutely no 1,2-pentanediol by-product was detected.

Comparative Example 1-1

Synthesis of 1,5-pentanediol

A hydrocracking catalyst was produced in the same manner as Example 1-1, except that the starting materials used were 44.4 mg (0.12 mmol) of iridium trichloride.n hydrate (Ishizu Shiyaku, iridium concentration: 53 mass %) and 104.1 mg (0.36 mmol) of potassium tetraoxorhenate(VII). The hydrocracking catalyst was used for reaction in the same manner as Example 1-2. As a result, the tetrahydrofurfuryl alcohol conversion rate was 39.3%, the 1,5-pentanediol yield was 27.1% and the selectivity was 69.0%. Absolutely no 1,2-pentanediol by-product was detected.

Example 1-4

Production of Hydrocracking Catalyst

A hydrocracking catalyst (hereunder also referred to as "Ir—Ru—Re catalyst (2)") was produced in the same manner as Example 1-1, except that in Example 1-1, 20.1 mg (0.060 mmol) of iridium tetrachloride was used instead of iridium trichloride.n hydrate, the amount of potassium perruthenate (VII) was changed to 12.3 mg (0.060 mmol) and the amount of potassium tetraoxorhenate(VII) was changed to 17.4 mg (0.060 mmol).

Example 1-5

Synthesis of 1,5-pentanediol

Reaction was carried out in the same manner as Example 1-3, except that in Example 1-2, the hydrocracking catalyst was changed to the one produced in Example 1-4, and the reaction temperature was changed to 80° C. As a result, the tetrahydrofurfuryl alcohol conversion rate was 48.7%, the 1,5-pentanediol yield was 49.4% and the selectivity was 88.6%. Absolutely no 1,2-pentanediol by-product was detected.

Example 1-6

Production of Hydrocracking Catalyst

A hydrocracking catalyst (hereunder also referred to as "Ir—Ru—Re catalyst (3)") was obtained in the same manner as Example 1-1, except that in Example 1-1, the amount of potassium perruthenate(VII) was changed to 38.8 mg (0.19 mmol) and the amount of potassium tetraoxorhenate(VII) was changed to 55.0 mg (0.19 mmol).

Example 1-7

Synthesis of 1,5-pentanediol

Reaction was carried out in the same manner as Example 1-2, except that in Example 1-2, the reaction temperature was changed from 120° C. to 60° C. and the hydrocracking catalyst was changed to the one produced in Example 1-6. As a result, the tetrahydrofurfuryl alcohol conversion rate was 45.1%, the 1,5-pentanediol yield was 42.3% and the selectivity was 93.9%. Absolutely no 1,2-pentanediol by-product was detected.

Example 1-8

Production of Hydrocracking Catalyst

A hydrocracking catalyst (hereunder also referred to as "Ir—Ru—Re catalyst (4)") was obtained in the same manner as Example 1-1, except that in Example 1-1, the amount of potassium tetraoxorhenate(VII) was changed to 55.0 mg (0.19 mmol).

Example 1-9

Synthesis of 1,5-pentanediol

Reaction was carried out in the same manner as Example 1-2, except that in Example 1-2, the reaction temperature was changed from 120° C. to 80° C., the hydrogen pressure was changed from 8 MPa to 2 MPa, and the hydrocracking catalyst was the one produced in Example 1-8. As a result, the tetrahydrofurfuryl alcohol conversion rate was 69.2%, the 1,5-pentanediol yield was 60.0% and the selectivity was 86.8%. Absolutely no 1,2-pentanediol by-product was detected.

Example 1-10

Synthesis of 1,5-pentanediol

Reaction was carried out in the same manner as Example 1-2, except that in Example 1-2, the reaction temperature was changed from 120° C. to 80° C., the hydrogen pressure was changed from 8 MPa to 0.5 MPa, and the hydrocracking catalyst was the one produced in Example 1-8. As a result, the tetrahydrofurfuryl alcohol conversion rate was 42.1%, the 1,5-pentanediol yield was 37.9% and the selectivity was 90.0%. Absolutely no 1,2-pentanediol by-product was detected.

Example 1-11

Production of Hydrocracking Catalyst

A hydrocracking catalyst (hereunder also referred to as "Rh—Ru—Re catalyst (1)") was produced in the same manner as Example 1-1, except that in Example 1-1, 15.8 mg (0.060 mmol) of rhodium trichloride.trihydrate was used instead of iridium trichloride.n hydrate, the amount of potassium perruthenate(VII) was changed to 12.3 mg (0.060 mmol) and the amount of potassium tetraoxorhenate(VII) was changed to 17.4 mg (0.060 mmol).

Example 1-12

Synthesis of 1,5-pentanediol

Reaction was carried out in the same manner as Example 1-2, except that in Example 1-2, the hydrocracking catalyst was changed to the one produced in Example 1-11. As a result, the tetrahydrofurfuryl alcohol conversion rate was 55.6%, the 1,5-pentanediol yield was 45.5% and the selectivity was 81.8%. The selectivity for 1,2-pentanediol by-product was 3.5%.

Comparative Example 1-2

Synthesis of 1,5-pentanediol

A hydrocracking catalyst was produced in the same manner as Example 1-1, except that the starting materials used were 31.6 mg (0.12 mmol) of rhodium trichloride.trihydrate and 104.1 mg (0.36 mmol) of potassium tetraoxorhenate (VII). Reaction was conducted in the same manner as Example 1-2 except for using this hydrocracking catalyst. As a result, the tetrahydrofurfuryl alcohol conversion rate was 13.9%, the 1,5-pentanediol yield was 13.1% and the selectivity was 94.2%. Absolutely no 1,2-pentanediol by-product was detected.

Example 1-13

Production of Hydrocracking Catalyst

A hydrocracking catalyst (hereunder also referred to as "Ru—Ru—Re catalyst (1)") was produced in the same manner as Example 1-1, except that in Example 1-1, 12.5 mg (0.06 mmol) of ruthenium trichloride was used instead of iridium trichloride.n hydrate, the amount of potassium perruthenate(VII) was changed to 12.3 mg (0.060 mmol) and the amount of potassium tetraoxorhenate(VII) was changed to 17.4 mg (0.060 mmol).

Example 1-14

Synthesis of 1,5-pentanediol

Reaction was carried out in the same manner as Example 1-2, except that in Example 1-2, the hydrocracking catalyst was changed to the one produced in Example 1-13. As a result, the tetrahydrofurfuryl alcohol conversion rate was 52.9%, the 1,5-pentanediol yield was 27.1% and the selectivity was 51.2%. The selectivity for 1,2-pentanediol by-product was 3.5%.

Comparative Example 1-3

Synthesis of 1,5-pentanediol

A hydrocracking catalyst was produced in the same manner as Example 1-1, except that the starting materials used were 24.9 mg (0.12 mmol) of ruthenium trichloride and 104.1 mg (0.36 mmol) of potassium tetraoxorhenate(VII). Reaction was conducted in the same manner as Example 1-2 except for using this hydrocracking catalyst. As a result, the tetrahydrofurfuryl alcohol conversion rate was 9.1%, the 1,5-pentanediol yield was 6.3% and the selectivity was 69.7%. Absolutely no 1,2-pentanediol by-product was detected.

Example 1-15

Production of Hydrocracking Catalyst

A hydrocracking catalyst (hereunder also referred to as "Pd—Ru—Re catalyst (1)") was produced in the same manner as Example 1-1, except that in Example 1-1, 21.3 mg (0.12 mmol) of palladium dichloride was used instead of iridium trichloride.n hydrate.

Example 1-16

Synthesis of 1,5-pentanediol

Reaction was carried out in the same manner as Example 1-2, except that in Example 1-2, the hydrocracking catalyst was changed to the one produced in Example 1-15. As a result, the tetrahydrofurfuryl alcohol conversion rate was 34.0%, the 1,5-pentanediol yield was 25.3% and the selectivity was 74.3%. Absolutely no 1,2-pentanediol by-product was detected.

Example 1-17

Production of Hydrocracking Catalyst

A hydrocracking catalyst (hereunder also referred to as "Pt—Ru—Re catalyst (1)") was produced in the same manner as Example 1-1, except that in Example 1-1, 16.0 mg (0.060 mmol) of platinum dichloride was used instead of iridium trichloride.n hydrate, the amount of potassium perruthenate(VII) was changed to 12.3 mg (0.060 mmol) and the amount of potassium tetraoxorhenate(VII) was changed to 17.4 mg (0.060 mmol).

Example 1-18

Synthesis of 1,5-pentanediol

Reaction was carried out in the same manner as Example 1-2, except that in Example 1-2, the hydrocracking catalyst was changed to the one produced in Example 1-17. As a result, the tetrahydrofurfuryl alcohol conversion rate was 65.2%, the 1,5-pentanediol yield was 52.0% and the selectivity was 79.7%. Absolutely no 1,2-pentanediol by-product was detected.

Example 1-19

Production of Hydrocracking Catalyst

A hydrocracking catalyst (hereunder also referred to as "Au—Ru—Re catalyst (1)") was produced in the same manner as Example 1-1, except that in Example 1-1, 47.3 mg (0.12 mmol) of auric chloride trihydrate was used instead of iridium trichloride.n hydrate.

Example 1-20

Synthesis of 1,5-pentanediol

Reaction was carried out in the same manner as Example 1-2, except that in Example 1-2, the hydrocracking catalyst was changed to the one produced in Example 1-19. As a result, the tetrahydrofurfuryl alcohol conversion rate was 18.7%, the 1,5-pentanediol yield was 14.9% and the selectivity was 79.7%. Absolutely no 1,2-pentanediol by-product was detected.

Example 1-21

Production of Hydrocracking Catalyst

A hydrocracking catalyst (hereunder also referred to as "La—Ru—Re catalyst (1)") was produced in the same manner as Example 1-1, except that in Example 1-1, 44.6 mg (0.12 mmol) of lanthanum trichloride heptahydrate was used instead of iridium trichloride.n hydrate.

Example 1-22

Synthesis of 1,5-pentanediol

Reaction was carried out in the same manner as Example 1-2, except that in Example 1-2, the hydrocracking catalyst was changed to the one produced in Example 1-21. As a result, the tetrahydrofurfuryl alcohol conversion rate was 15.5%, the 1,5-pentanediol yield was 12.5% and the selectivity was 80.2%. Absolutely no 1,2-pentanediol by-product was detected.

Example 1-23

Production of Hydrocracking Catalyst

A hydrocracking catalyst (hereunder also referred to as "Yb—Ru—Re catalyst (1)") was produced in the same manner as Example 1-1, except that in Example 1-1, 46.5 mg (0.12 mmol) of ytterbium trichloride hexahydrate was used instead of iridium trichloride.n hydrate.

Example 1-24

Synthesis of 1,5-pentanediol

Reaction was carried out in the same manner as Example 1-2, except that in Example 1-2, the hydrocracking catalyst was changed to the one produced in Example 1-23. As a result, the tetrahydrofurfuryl alcohol conversion rate was 10.8%, the 1,5-pentanediol yield was 7.5% and the selectivity was 70.0%. Absolutely no 1,2-pentanediol by-product was detected.

Example 1-25

Production of Hydrocracking Catalyst

A hydrocracking catalyst (hereunder also referred to as "Zr—Ru—Re catalyst (1)") was produced in the same manner as Example 1-1, except that in Example 1-1, 28.0 mg (0.12 mmol) of zirconium tetrachloride was used instead of iridium trichloride.n hydrate.

Example 1-26

Synthesis of 1,5-pentanediol

Reaction was carried out in the same manner as Example 1-2, except that in Example 1-2, the hydrocracking catalyst was changed to the one produced in Example 1-25. As a result, the tetrahydrofurfuryl alcohol conversion rate was 35.1%, the 1,5-pentanediol yield was 21.3% and the selectivity was 60.7%. Absolutely no 1,2-pentanediol by-product was detected.

Example 1-27

Production of Hydrocracking Catalyst

A hydrocracking catalyst (hereunder also referred to as "Hf—Ru—Re catalyst (1)") was produced in the same manner as Example 1-1, except that in Example 1-1, 38.4 mg (0.12 mmol) of hafnium tetrachloride was used instead of iridium trichloride.n hydrate.

Example 1-28

Synthesis of 1,5-pentanediol

Reaction was carried out in the same manner as Example 1-2, except that in Example 1-2, the hydrocracking catalyst was changed to the one produced in Example 1-27. As a result, the tetrahydrofurfuryl alcohol conversion rate was 31.4%, the 1,5-pentanediol yield was 16.6% and the selectivity was 53.0%. Absolutely no 1,2-pentanediol by-product was detected.

Example 1-29

Production of Hydrocracking Catalyst

A hydrocracking catalyst (hereunder also referred to as "Nb—Ru—Re catalyst (1)") was produced in the same manner as Example 1-1, except that in Example 1-1, 32.4 mg (0.12 mmol) of niobium pentachloride was used instead of iridium trichloride.n hydrate.

Example 1-30

Synthesis of 1,5-pentanediol

Reaction was carried out in the same manner as Example 1-2, except that in Example 1-2, the hydrocracking catalyst was changed to the one produced in Example 1-29. As a result, the tetrahydrofurfuryl alcohol conversion rate was 39.4%, the 1,5-pentanediol yield was 27.0% and the selectivity was 68.5%. Absolutely no 1,2-pentanediol by-product was detected.

Example 1-31

Production of Hydrocracking Catalyst

A hydrocracking catalyst (hereunder also referred to as "Ta—Ru—Re catalyst (1)") was produced in the same manner as Example 1-1, except that in Example 1-1, 43.0 mg (0.12 mmol) of tantalum pentachloride was used instead of iridium trichloride.n hydrate.

Example 1-32

Synthesis of 1,5-pentanediol

Reaction was carried out in the same manner as Example 1-2, except that in Example 1-2, the hydrocracking catalyst was changed to the one produced in Example 1-31. As a result, the tetrahydrofurfuryl alcohol conversion rate was 43.8%, the 1,5-pentanediol yield was 28.5% and the selectivity was 65.1%. Absolutely no 1,2-pentanediol by-product was detected.

Example 1-33

Production of Hydrocracking Catalyst

A hydrocracking catalyst (hereunder also referred to as "Mo—Ru—Re catalyst (1)") was produced in the same manner as Example 1-1, except that in Example 1-1, 32.8 mg (0.12 mmol) of molybdenum pentachloride was used instead of iridium trichloride.n hydrate.

Example 1-34

Synthesis of 1,5-pentanediol

Reaction was carried out in the same manner as Example 1-2, except that in Example 1-2, the hydrocracking catalyst was changed to the one produced in Example 1-33. As a result, the tetrahydrofurfuryl alcohol conversion rate was 5.6%, the 1,5-pentanediol yield was 4.6% and the selectivity was 82.9%. Absolutely no 1,2-pentanediol by-product was detected.

Example 1-35

Production of Hydrocracking Catalyst

A hydrocracking catalyst (hereunder also referred to as "W—Ru—Re catalyst (1)") was produced in the same manner as Example 1-1, except that in Example 1-1, 39.1 mg (0.12 mmol) of tungsten tetrachloride was used instead of iridium trichloride.n hydrate.

Example 1-36

Synthesis of 1,5-pentanediol

Reaction was carried out in the same manner as Example 1-2, except that in Example 1-2, the hydrocracking catalyst was changed to the one produced in Example 1-35. As a result, the tetrahydrofurfuryl alcohol conversion rate was 36.2%, the 1,5-pentanediol yield was 21.6% and the selectivity was 59.8%. Absolutely no 1,2-pentanediol by-product was detected.

Comparative Example 1-4

Synthesis of 1,5-pentanediol

A hydrocracking catalyst was produced in the same manner as Example 1-1, except that the starting materials used were 39.1 mg (0.12 mmol) of tungsten tetrachloride and 34.7 mg (0.12 mmol) of potassium tetraoxorhenate(VII). Reaction was conducted in the same manner as Example 1-2 except for using this hydrocracking catalyst. As a result, the tetrahydrofurfuryl alcohol conversion rate was 0.12%, and absolutely no 1,5-pentanediol was produced.

Comparative Example 1-5

Synthesis of 1,5-pentanediol

A hydrocracking catalyst was produced in the same manner as Example 1-1, except that the starting materials used were 24.5 mg (0.12 mmol) of potassium perruthenate(VII) and 34.7 mg (0.12 mmol) of potassium tetraoxorhenate(VII). Reaction was conducted in the same manner as Example 1-2 except for using this hydrocracking catalyst. As a result, the tetrahydrofurfuryl alcohol conversion rate was 2.3%, the 1,5-pentanediol yield was 1.9% and the selectivity was 82.9%.

Example 1-37

Production of Hydrocracking Catalyst

A hydrocracking catalyst (hereunder also referred to as "Mn—Ru—Re catalyst (1)") was produced in the same manner as Example 1-1, except that in Example 1-1, 23.7 mg (0.12 mmol) of manganese dichloride hexahydrate was used instead of iridium trichloride.n hydrate.

Example 1-38

Synthesis of 1,5-pentanediol

Reaction was carried out in the same manner as Example 1-2, except that in Example 1-2, the hydrocracking catalyst was changed to the one produced in Example 1-37. As a result, the tetrahydrofurfuryl alcohol conversion rate was 8.8%, the 1,5-pentanediol yield was 3.6% and the selectivity was 41.5%. Absolutely no 1,2-pentanediol by-product was detected.

Example 1-39

Production of Hydrocracking Catalyst

A hydrocracking catalyst (hereunder also referred to as "Re—Ru—Re catalyst (1)") was produced in the same manner as Example 1-1, except that in Example 1-1, 21.8 mg (0.060 mmol) of rhenium pentachloride was used instead of iridium trichloride.n hydrate, the amount of potassium perruthenate(VII) was changed to 12.3 mg (0.060 mmol) and the amount of potassium tetraoxorhenate(VII) was changed to 17.4 mg (0.060 mmol).

Example 1-40

Synthesis of 1,5-pentanediol

Reaction was carried out in the same manner as Example 1-2, except that in Example 1-2, the hydrocracking catalyst was changed to the one produced in Example 1-39. As a result, the tetrahydrofurfuryl alcohol conversion rate was 77.4%, the 1,5-pentanediol yield was 40.4% and the selectivity was 52.2%. Absolutely no 1,2-pentanediol by-product was detected.

Example 1-41

Synthesis of 1,5-pentanediol

Reaction was carried out in the same manner as Example 1-2, except that in Example 1-2, the hydrocracking catalyst was changed to the one produced in Example 1-39, and the reaction temperature during reduction treatment was changed from 120° C. to 80° C. As a result, the tetrahydrofurfuryl alcohol conversion rate was 13.7%, the 1,5-pentanediol yield was 12.1% and the selectivity was 88.1%. Absolutely no 1,2-pentanediol by-product was detected.

Example 1-42

Production of Hydrocracking Catalyst

A hydrocracking catalyst (hereunder also referred to as "Co—Ru—Re catalyst (1)") was produced in the same manner as Example 1-1, except that in Example 1-1, 28.6 mg (0.12 mmol) of cobalt dichloride hexahydrate was used instead of iridium trichloride.n hydrate.

Example 1-43

Synthesis of 1,5-pentanediol

Reaction was carried out in the same manner as Example 1-2, except that in Example 1-2, the hydrocracking catalyst was changed to the one produced in Example 1-42, and the reaction temperature was changed from 120° C. to 150° C. As a result, the tetrahydrofurfuryl alcohol conversion rate was 26.3%, the 1,5-pentanediol yield was 13.4% and the selectivity was 51.0%. Absolutely no 1,2-pentanediol by-product was detected.

Example 1-44

Production of Hydrocracking Catalyst

A hydrocracking catalyst (hereunder also referred to as "Cu—Ru—Re catalyst (1)") was produced in the same manner as Example 1-1, except that in Example 1-1, 16.1 mg (0.12 mmol) of copper dichloride hexahydrate was used instead of iridium trichloride.n hydrate.

Example 1-45

Synthesis of 1,5-pentanediol

Reaction was carried out in the same manner as Example 1-2, except that in Example 1-2, the hydrocracking catalyst was changed to the one produced in Example 1-44, and the reaction temperature was changed from 120° C. to 150° C. As a result, the tetrahydrofurfuryl alcohol conversion rate was 20.9%, the 1,5-pentanediol yield was 10.8% and the selectivity was 51.9%. Absolutely no 1,2-pentanediol by-product was detected.

Example 1-46

Production of Hydrocracking Catalyst

A hydrocracking catalyst (hereunder also referred to as "Ag—Ru—Re catalyst (1)") was produced in the same manner as Example 1-1, except that in Example 1-1, 17.2 mg (0.12 mmol) of silver chloride was used instead of iridium trichloride.n hydrate, the amount of potassium perruthenate(VII) was changed to 12.3 mg (0.060 mmol) and the amount of potassium tetraoxorhenate(VII) was changed to 17.4 mg (0.060 mmol).

Example 1-47

Synthesis of 1,5-pentanediol

Reaction was carried out in the same manner as Example 1-2, except that in Example 1-2, the hydrocracking catalyst was changed to the one produced in Example 1-46. As a result, the tetrahydrofurfuryl alcohol conversion rate was 7.1%, the 1,5-pentanediol yield was 5.4% and the selectivity was 75.5%. Absolutely no 1,2-pentanediol by-product was detected.

Example 1-48

Production of Hydrocracking Catalyst

A hydrocracking catalyst (hereunder also referred to as "Ir—Ru—Re catalyst (5)") was produced in the same manner as Example 1-1, except that in Example 1-1, 42.2 mg (0.12 mmol) of tetrapropylammonium ruthenate was used instead of potassium perruthenate.

Example 1-49

Synthesis of 1,5-pentanediol

Reaction was carried out in the same manner as Example 1-2, except that in Example 1-2, the hydrocracking catalyst was changed to the one produced in Example 1-48, and the reaction temperature was changed from 120° C. to 80° C. As a result, the tetrahydrofurfuryl alcohol conversion rate was 78.0%, the 1,5-pentanediol yield was 65.8% and the selectivity was 84.3%. Absolutely no 1,2-pentanediol by-product was detected.

Example 1-50

Production of Hydrocracking Catalyst

A hydrocracking catalyst (hereunder also referred to as "Ir—Ru—Re catalyst (6)") was produced in the same manner as Example 1-1, except that in Example 1-1, 19.8 mg (0.12 mmol) of ruthenium tetraoxide was used instead of potassium perruthenate.

Example 1-51

Synthesis of 1,5-pentanediol

Reaction was carried out in the same manner as Example 1-2, except that in Example 1-2, the hydrocracking catalyst was changed to the one produced in Example 1-50, and the reaction temperature was changed from 120° C. to 80° C. As a result, the tetrahydrofurfuryl alcohol conversion rate was 86.5%, the 1,5-pentanediol yield was 68.0% and the selectivity was 84.3%. Absolutely no 1,2-pentanediol by-product was detected.

Example 1-52

Production of Hydrocracking Catalyst

A hydrocracking catalyst (hereunder also referred to as "Ir—Ru—Re catalyst (7)") was produced in the same manner as Example 1-1, except that in Example 1-1, the amount of iridium trichloride.n hydrate used was changed to 22.2 mg (0.060 mmol) and the amount of potassium perruthenate(VII) used was changed to 12.3 mg (0.060 mmol), and 16.1 mg (0.060 mmol) of ammonium tetraoxorhenate(VII) was used instead of potassium tetraoxorhenate(VII).

Example 1-53

Synthesis of 1,5-pentanediol

Reaction was carried out in the same manner as Example 1-2, except that in Example 1-2, the hydrocracking catalyst was changed to the one produced in Example 1-52, and the reaction temperature was changed from 120° C. to 80° C. As a result, the tetrahydrofurfuryl alcohol conversion rate was 57.3%, the 1,5-pentanediol yield was 45.7% and the selectivity was 79.7%. Absolutely no 1,2-pentanediol by-product was detected.

Example 1-54

Production of Hydrocracking Catalyst

A hydrocracking catalyst (hereunder also referred to as "Ir—Ru—Re catalyst (8)") was produced in the same manner as Example 1-1, except that in Example 1-1, the amount of iridium trichloride.n hydrate used was changed to 22.2 mg (0.060 mmol) and the amount of potassium perruthenate(VII) used was changed to 12.3 mg (0.060 mmol), and 14.5 mg (0.030 mmol) of dirhenium heptoxide was used instead of potassium tetraoxorhenate(VII).

Example 1-55

Synthesis of 1,5-pentanediol

Reaction was carried out in the same manner as Example 1-2, except that in Example 1-2, the hydrocracking catalyst was changed to the one produced in Example 1-54, and the reaction temperature was changed from 120° C. to 80° C. As a result, the tetrahydrofurfuryl alcohol conversion rate was 56.3%, the 1,5-pentanediol yield was 43.4% and the selectivity was 77.1%. Absolutely no 1,2-pentanediol by-product was detected.

Example 1-56

Production of Hydrocracking Catalyst

A hydrocracking catalyst (hereunder also referred to as "Ir—Ru—Mo catalyst (1)") was produced in the same manner as Example 1-1, except that in Example 1-1, 29.6 mg (0.122 mmol) of sodium tetraoxomolybdate(VI) dihydrate was used instead of potassium tetraoxorhenate(VII).

Example 1-57

Synthesis of 1,5-pentanediol

Reaction was carried out in the same manner as Example 1-2, except that in Example 1-2, the hydrocracking catalyst was changed to the one produced in Example 1-56, and the reaction temperature was changed from 120° C. to 80° C. As a result, the tetrahydrofurfuryl alcohol conversion rate was 16.5%, the 1,5-pentanediol yield was 15.7% and the selectivity was 95.0%. Absolutely no 1,2-pentanediol by-product was detected.

Example 1-58

Production of Hydrocracking Catalyst

A hydrocracking catalyst (hereunder also referred to as "Ir—Ru—W catalyst (1)") was produced in the same manner as Example 1-1, except that in Example 1-1, 39.6 mg (0.12 mmol) of sodium tetraoxotungstate(VI) dihydrate was used instead of potassium tetraoxorhenate(VII).

Example 1-59

Synthesis of 1,5-pentanediol

Reaction was carried out in the same manner as Example 1-2, except that in Example 1-2, the hydrocracking catalyst was changed to the one produced in Example 1-58, and the reaction temperature was changed from 120° C. to 80° C. As a result, the tetrahydrofurfuryl alcohol conversion rate was 21.4%, the 1,5-pentanediol yield was 20.2% and the selectivity was 94.3%. Absolutely no 1,2-pentanediol by-product was detected.

Example 1-60

Synthesis of 1,5-pentanediol

Reaction was conducted in the same manner as Example 1-2, except that in Example 1-2, the hydrocracking catalyst produced in Example 1-1 was rinsed 5 times with 1,2-diethoxyethane before synthesizing the 1,5-pentanediol, 5.00 g (2.45 mmol) of a 5% tetrahydrofurfuryl alcohol.1,2-diethoxyethane solution was used instead of the 5% tetrahydrofurfuryl alcohol water-soluble solution, and the reaction temperature was changed from 120° C. to 80° C. As a result, the tetrahydrofurfuryl alcohol conversion rate was 36.3%, the 1,5-pentanediol yield was 30.8% and the selectivity was 85.0%. Absolutely no 1,2-pentanediol by-product was detected. The "5% tetrahydrofurfuryl alcohol 1,2-diethoxyethane solution" was a solution containing 5 mass % tetrahydrofurfuryl alcohol in 1,2-diethoxyethane, based on the total solution.

Example 1-61

Synthesis of 1,5-pentanediol

Reaction was conducted in the same manner as Example 1-2, except that in Example 1-2, the hydrocracking catalyst produced in Example 1-1 was rinsed 5 times with cyclohexane before synthesizing the 1,5-pentanediol, 5.00 g (2.45 mmol) of a 5% tetrahydrofurfuryl alcohol.cyclohexane solution was used instead of the 5% tetrahydrofurfuryl alcohol water-soluble solution, and the reaction temperature was changed from 120° C. to 80° C. As a result, the tetrahydrofurfuryl alcohol conversion rate was 87.9%, the 1,5-pentanediol yield was 22.3% and the selectivity was 25.4%. Absolutely no 1,2-pentanediol by-product was detected. The "5% tetrahydrofurfuryl alcohol cyclohexane solution" was a solution containing 5 mass % tetrahydrofurfuryl alcohol in cyclohexane, based on the total solution.

Example 1-62

Synthesis of 1,5-pentanediol

Reaction was conducted in the same manner as Example 1-2, except that in Example 1-2, the 5% tetrahydrofurfuryl alcohol water-soluble solution was changed to 6.13 g (60.0 mmol) of tetrahydrofurfuryl alcohol. As a result, the tetrahydrofurfuryl alcohol conversion rate was 40.0%, the 1,5-pentanediol yield was 31.5% and the selectivity was 78.7%. Absolutely no 1,2-pentanediol by-product was detected.

Example 1-63 (Production of Hydrocracking Catalyst) and Example 1-64 (Synthesis of 1,5-pentanediol)

After adding 17.4 mg (0.052 mmol) of iridium tetrachloride (product of Wako Pure Chemical Industries, Ltd., purity: >99.5 mass %), 10.6 mg (0.052 mmol) of potassium perruthenate(VII) and 2 ml of water into an autoclave equipped with a 50 ml glass inner cylindrical tube, the mixture was heated and stirred at 120° C. for 30 minutes. The solution was temporarily cooled to room temperature. After adding 0.25 g of silica ($SiO_2$; product of Fuji Silysia Chemical, Ltd., trade name: CARiACT G-6) to the cooled solution, it was concentrated under reduced pressure at 60° C. to distill off the solvent. The obtained residue was further dried under reduced pressure at 60° C. for 8 hours to obtain 252 mg of a solid having 4 mass % iridium and 2 mass % ruthenium supported on silica (hereunder also referred to as "Ir—Ru/$SiO_2$").

After then placing 25 mg of the obtained solid "Ir—Ru/$SiO_2$", 1.3 mg (0.0026 mmol) of dirhenium heptoxide and 5.00 g (2.45 mmol) of a 5% tetrahydrofurfuryl alcohol water-soluble solution in an autoclave equipped with a glass inner cylindrical tube, it was pressurized to 8 MPa with hydrogen gas and reacted at 120° C. for 2 hours while stirring. The solid ("Ir—Ru/$SiO_2$") and dirhenium heptoxide were mixed and the mixture was reduced by the hydrogen, thereby producing a hydrocracking catalyst having iridium, ruthenium, and rhenium supported on silica (hereunder also referred to as "Ir—Ru—Re/$SiO_2$ catalyst (1))". Also, contacting tetrahydrofurfuryl alcohol with the produced hydrocracking catalyst in the presence of hydrogen gas promoted hydrocracking reaction.

The obtained filtrate was analyzed by gas chromatography, resulting in a tetrahydrofurfuryl alcohol conversion rate of 44.6%, a 1,5-pentanediol yield of 36.2% and a selectivity of 81.2%. Absolutely no 1,2-pentanediol by-product was detected.

Example 1-65

Production of Hydrocracking Catalyst

After adding 17.4 mg (0.052 mmol) of iridium tetrachloride (product of Wako Pure Chemical Industries, Ltd., purity: >99.5 mass %), 10.6 mg (0.052 mmol) of potassium perruthenate(VII), 12.6 mg (0.026 mmol) of dirhenium heptoxide and 2 ml of water into an autoclave equipped with a 50 ml glass inner cylindrical tube, the mixture was heated and stirred at 120° C. for 30 minutes. The obtained solution was then temporarily cooled to room temperature. After adding 0.25 g of silica ($SiO_2$, product of Fuji Silysia Chemical, Ltd., trade name: CARiACT G-6) to the cooled solution, it was concentrated under reduced pressure at 60° C. to distill off the solvent. The obtained residue was further dried under reduced pressure at 60° C. for 8 hours to obtain a hydrocracking catalyst having 4 mass % of iridium, 2 mass % of ruthenium and 4 mass % of rhenium supported on silica (hereunder also referred to as "Ir—Ru—Re/$SiO_2$ (1)"). The loading weight of each protein is the amount based on the support (silica). This also applies throughout the following examples and comparative examples.

Example 1-66

Synthesis of 1,5-pentanediol

Reaction was carried out in the same manner as Example 1-2, except that in Example 1-2, the hydrocracking catalyst was changed to 25 mg of the catalyst produced in Example 1-65. As a result, the tetrahydrofurfuryl alcohol conversion rate was 70.9%, the 1,5-pentanediol yield was 52.3% and the selectivity was 73.8%. Absolutely no 1,2-pentanediol by-product was detected.

Example 1-67

Synthesis of 1,5-pentanediol

Reaction was carried out in the same manner as Example 1-2, except that in Example 1-2, the hydrocracking catalyst was changed to 25 mg of the catalyst produced in Example 1-65, and the reaction temperature was changed from 120° C. to 110° C. As a result, the tetrahydrofurfuryl alcohol conversion rate was 38.8%, the 1,5-pentanediol yield was 35.6% and the selectivity was 91.7%. Absolutely no 1,2-pentanediol by-product was detected.

Example 1-68

Synthesis of 1,5-pentanediol

Reaction was carried out in the same manner as Example 1-2, except that in Example 1-2, the hydrocracking catalyst was changed to 25 mg of the catalyst produced in Example 1-65, and the reaction temperature was changed from 120° C. to 100° C. As a result, the tetrahydrofurfuryl alcohol conversion rate was 24.5%, the 1,5-pentanediol yield was 22.6% and the selectivity was 92.4%. Absolutely no 1,2-pentanediol by-product was detected.

Example 1-69

Production of Hydrocracking Catalyst

A hydrocracking catalyst (hereunder also referred to as "Ir—Ru—Re/SiO$_2$ catalyst (2)") was produced in the same manner as Example 1-65, except that in Example 1-65, 18.3 mg (0.052 mmol) of tetrapropylammonium perruthenate was used instead of potassium perruthenate(VII).

Example 1-70

Synthesis of 1,5-pentanediol

Reaction was carried out in the same manner as Example 1-2, except that in Example 1-2, the hydrocracking catalyst was changed to 25 mg of the catalyst produced in Example 1-69. As a result, the tetrahydrofurfuryl alcohol conversion rate was 70.1%, the 1,5-pentanediol yield was 52.9% and the selectivity was 75.5%. Absolutely no 1,2-pentanediol by-product was detected.

Example 1-71

Production of Hydrocracking Catalyst

A hydrocracking catalyst (hereunder also referred to as "Ir—Ru—Re catalyst (9)") was produced in the same manner as Example 1-1, except that in Example 1-1, the amount of iridium trichloride.n hydrate used was changed to 39.2 mg (0.11 mmol), the amount of potassium perruthenate(VII) used was changed to 22.1 mg (0.11 mmol), and the amount of potassium tetraoxorhenate(VII) used was changed to 31.2 mg (0.11 mmol).

Example 1-72

Synthesis of 1,6-hexanediol

[Chemical Formula 24]

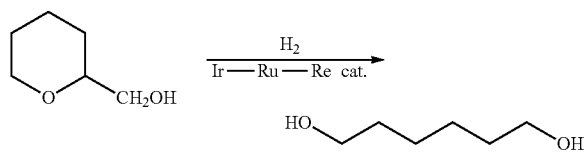

Reaction was carried out in the same manner as Example 1-2, except that in Example 1-2, the hydrocracking catalyst was changed to the one produced in Example 1-71, the 5% tetrahydrofurfuryl alcohol water-soluble solution was changed to a 5% tetrahydropyran-2-methanol water-soluble solution (2.15 mmol), and the reaction temperature was changed from 120° C. to 80° C. This caused the chemical reaction represented above to proceed. As a result, the tetrahydropyran-2-methanol conversion rate was 41.3%, the 1,6-hexanediol yield was 31.9% and the selectivity was 77.3%. Absolutely no 1,2-hexanediol by-product was detected. The "5% tetrahydropyran-2-methanol water-soluble solution" was a water-soluble solution containing 5 mass % of tetrahydropyran-2-methanol based on the total water-soluble solution.

Example 1-73

Production of Hydrocracking Catalyst

A hydrocracking catalyst (hereunder also referred to as "Ir—Ru—Re catalyst (10)") was produced in the same manner as Example 1-1, except that in Example 1-1, the amount of iridium trichloride.n hydrate used was changed to 50.2 mg (0.14 mmol), the amount of potassium perruthenate(VII) used was changed to 28.4 mg (0.14 mmol), and the amount of potassium tetraoxorhenate(VII) used was changed to 40.2 mg (0.14 mmol).

Example 1-74

Synthesis of ethanol

[Chemical Formula 25]

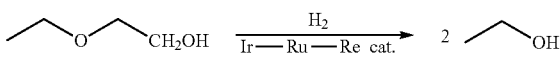

Reaction was carried out in the same manner as Example 1-2, except that in Example 1-2, the hydrocracking catalyst was changed to the one produced in Example 1-73, the 5% tetrahydrofurfuryl alcohol water-soluble solution was changed to a 5% 2-ethoxyethanol aqueous solution (2.77 mmol), and the reaction temperature was changed from 120° C. to 80° C. This caused the chemical reaction represented above to proceed. As a result, the 2-ethoxyethanol conversion rate was 64.9%, the ethanol yield was 64.1% and the selectivity was 98.8%. Absolutely no ethylene glycol by-product was detected. The "5% 2-ethoxyethanol water-soluble solution" was a water-soluble solution containing 5 mass % of 2-ethoxyethanol based on the total water-soluble solution.

Example 1-75

Production of Hydrocracking Catalyst

After adding 40.1 mg (0.104 mmol) of dipotassium tetraoxoruthenate(VI) monohydrate (product of Soekawa Chemical Co., Ltd., ruthenium concentration: 26.2 mass %) and 1.0 g of water to a 10 ml volumetric flask, the mixture was heated and stirred at 70° C. for 1 hour. To this there were added 34.9 mg (0.104 mmol) of iridium tetrachloride and 1.0 g of water, and the mixture was again heated and stirred at 70° C. for 1 hour. To this there was added 0.50 g of silica (SiO$_2$; product of Fuji Silysia Chemical, Ltd., trade name: CARiACT G-6) and the mixture was further heated and stirred at 70° C. for 1 hour. Next, the solvent was distilled off under reduced pressure with an evaporator and the obtained residue was dried at 110° C. for 7 hours. After impregnating this with a solution of 27.9 mg (0.104 mmol) of ammonium tetraoxorhenate(VII) dissolved in 0.4 g of water, it was dried at 110° C. for 7 hours and at 250° C. for 4 hours, to obtain 560 mg of a solid comprising 4 mass % of iridium, 2.1 mass % of ruthenium and 3.9 mass % of rhenium supported on silica (hereunder also referred to as "Ir—Ru—Re/SiO$_2$ catalyst (3)").

Example 1-76

Synthesis of 1,5-pentanediol

After then placing 25 mg of the Ir—Ru—Re/SiO$_2$ catalyst (3) obtained in Example 1-75 and 5.00 g (2.45 mmol) of a 5% tetrahydrofurfuryl alcohol water-soluble solution in an autoclave equipped with a 50 ml glass inner cylindrical tube, it was pressurized to 8 MPa with hydrogen gas and then reacted at 120° C. for 2 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 54.8%, a 1,5-pentanediol yield of 47.4% and a selectivity of 86.5%. Absolutely no 1,2-pentanediol by-product was detected.

Example 1-77

Production of Hydrocracking Catalyst

After adding 40.1 mg (0.104 mmol) of dipotassium tetraoxoruthenate(VI) monohydrate (product of Soekawa Chemical Co., Ltd., ruthenium concentration: 26.2 mass %) and 1.0 g of water to a 10 ml volumetric flask, the mixture was heated and stirred at 70° C. for 1 hour. To this there were added 34.9 mg (0.104 mmol) of iridium tetrachloride and 1.0 g of water, and the mixture was again heated and stirred at 70° C. for 1 hour. To this there was added 0.50 g of silica ($SiO_2$, product of Fuji Silysia Chemical, Ltd., trade name: CARiACT G-6) and the mixture was further heated and stirred at 70° C. for 1 hour. The solvent was then distilled off under reduced pressure with an evaporator and the obtained residue was dried at 110° C. for 7 hours and at 250° C. for 4 hours, to obtain 560 mg of a solid comprising 4 mass % of iridium and 2.1 mass % of ruthenium supported on silica (hereunder also referred to as "Ir—Ru/$SiO_2$ catalyst (2)").

Example 1-78

Synthesis of 1,5-pentanediol

After placing 25 mg of the solid obtained in Example 1-77 (Ir—Ru/$SiO_2$ catalyst (2)), 5.00 g (2.45 mmol) of a 5% tetrahydrofurfuryl alcohol water-soluble solution and 1.26 mg (0.0026 mmol) of dirhenium heptoxide in the same apparatus as Example 1-76, the mixture was pressurized to 8 MPa with hydrogen gas and then reacted at 120° C. for 2 hours while stirring to obtain a reaction mixture. Mixture of the solid (Ir—Ru/$SiO_2$ catalyst (2)) and dirhenium heptoxide and reduction treatment with hydrogen produced a hydrocracking catalyst (hereunder also referred to as "Ir—Ru—Re/$SiO_2$ catalyst (4)"). Contacting this hydrocracking catalyst with tetrahydrofurfuryl alcohol in the presence of hydrogen gas promoted hydrocracking reaction.

Upon completion of the reaction, the obtained reaction mixture was cooled to room temperature and then filtered with an injector equipped with a membrane filter (0.45 μm). The obtained filtrate was analyzed by gas chromatography, resulting in a tetrahydrofurfuryl alcohol conversion rate of 36.2%, a 1,5-pentanediol yield of 30.8% and a selectivity of 85.0%. Absolutely no 1,2-pentanediol by-product was detected.

Example 1-79

Production of Hydrocracking Catalyst

After impregnating 0.50 g of silica ($SiO_2$; product of Fuji Silysia Chemical, Ltd., trade name: CARiACT G-6) with a water-soluble solution comprising 0.244 g (0.104 mmol) of a dipotassium tetraoxoruthenate(VI) water-soluble solution (product of Furuya Metal Co., Ltd., ruthenium concentration: 4.3 mass %) added to 0.2 g of water, the mixture was dried at 110° C. for 7 hours. Next, a water-soluble solution of 53.0 mg (0.104 mmol) of iridium hexachloride (product of Wako Pure Chemical Industries, Ltd., iridium concentration: 37.7%) dissolved in 0.4 g of water was further impregnated into the silica and dried at 110° C. for 7 hours to obtain a powder. The powder was dried at 250° C. for 4 hours to obtain 568 mg of a solid comprising 4 mass % of iridium and 2.1 mass % of ruthenium supported on silica (hereunder also referred to as "Ir—Ru/$SiO_2$ catalyst (3)").

Example 1-80

Synthesis of 1,5-pentanediol

After placing 25 mg of the (Ir—Ru/$SiO_2$ catalyst (3)) obtained in Example 1-79, 5.00 g (2.45 mmol) of a 5% tetrahydrofurfuryl alcohol water-soluble solution and 1.26 mg (0.0026 mmol) of dirhenium heptoxide in the same apparatus as Example 1-76, the mixture was pressurized to 8 MPa with hydrogen gas and then reacted at 120° C. for 2 hours while stirring. The solid (Ir—Ru/$SiO_2$ catalyst (3)) and dirhenium heptoxide were mixed and reduced by the hydrogen, thereby producing a hydrocracking catalyst having iridium, ruthenium and rhenium supported on silica (hereunder also referred to as ("Ir—Ru—Re/$SiO_2$ catalyst (5)")), and contact of the catalyst with the tetrahydrofurfuryl alcohol in the presence of the hydrogen gas promoted hydrocracking reaction.

Upon completion of the reaction, the obtained reaction mixture was cooled to room temperature and then filtered with an injector equipped with a membrane filter (0.45 μm). The obtained filtrate was analyzed by gas chromatography, resulting in a tetrahydrofurfuryl alcohol conversion rate of 69.7%, a 1,5-pentanediol yield of 57.2% and a selectivity of 82.1%. Absolutely no 1,2-pentanediol by-product was detected.

Example 1-81

Production of Hydrocracking Catalyst

After impregnating 0.50 g of silica ($SiO_2$; product of Fuji Silysia Chemical, Ltd., trade name: CARiACT G-6) with a water-soluble solution obtained by combining 0.244 g (0.104 mmol) of a dipotassium tetraoxoruthenate(VI) water-soluble solution (product of Furuya Metal Co., Ltd., ruthenium concentration: 4.3 mass %) and 0.2 g of water, the mixture was dried at 110° C. for 7 hours. Next, a water-soluble solution of 53.0 mg (0.104 mmol) of iridium hexachloride (product of Wako Pure Chemical Industries, Ltd., iridium concentration: 37.7 mass %) dissolved in 0.4 g of water was further impregnated into the silica and dried at 110° C. for 7 hours. After drying, a solution obtained by dissolving 27.9 mg (0.104 mmol) of ammonium tetraoxorhenate(VII) in 0.4 g of water was further impregnated therein and dried at 110° C. for 7 hours. The powder was dried at 250° C. for 4 hours to obtain 575 mg of a solid comprising 4 mass % of iridium, 2.1 mass % of ruthenium and 3.9 mass % of rhenium supported on silica (hereunder also referred to as "Ir—Ru—Re/$SiO_2$ catalyst (6)").

Example 1-82

Synthesis of 1,5-pentanediol

After placing 25 mg of the solid obtained in Example 1-81 (Ir—Ru—Re/$SiO_2$ catalyst (6)) and 5.00 g (2.45 mmol) of a 5% tetrahydrofurfuryl alcohol water-soluble solution in the same apparatus as Example 1-76, the mixture was pressurized to 8 MPa with hydrogen gas and reaction was conducted at 120° C. for 2 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 59.1%, a 1,5-pentanediol yield of 49.8% and a selectivity of 84.3%. Absolutely no 1,2-pentanediol by-product was detected.

Example 1-83

Synthesis of 1,5-pentanediol

After placing 307 mg of a solid obtained by the same method as Example 1-81 (Ir—Ru—Re/SiO$_2$ catalyst (6)) and 10.0 g (4.90 mmol) of a 5% tetrahydrofurfuryl alcohol water-soluble solution in the same apparatus as Example 1-76, the mixture was pressurized to 1 MPa with hydrogen gas and then heated and stirred at 120° C. for 1 hour while stirring. The suspension was subjected to centrifugal separation to remove the liquid layer. After placing 3.07 g (30.1 mmol) of a tetrahydrofurfuryl alcohol water-soluble solution on the residue, it was pressurized to 8 MPa with hydrogen gas and then reaction was conducted at 120° C. for 4 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 82.6%, a 1,5-pentanediol yield of 60.7% and a selectivity of 73.5%. Absolutely no 1,2-pentanediol by-product was detected.

Example 1-84

Synthesis of 1,5-pentanediol

After placing 154 mg of a solid obtained by the same method as Example 1-81 (Ir—Ru—Re/SiO$_2$ catalyst (6)) and 7.50 g (3.68 mmol) of a 5% tetrahydrofurfuryl alcohol water-soluble solution in the same apparatus as Example 1-76, the mixture was pressurized to 1 MPa with hydrogen gas and then heated and stirred at 120° C. for 1 hour while stirring. The suspension obtained in this manner was subjected to centrifugal separation to remove the liquid layer, and obtain a residue. After placing 3.19 g (15.6 mmol) of a 50% tetrahydrofurfuryl alcohol water-soluble solution on the residue, it was pressurized to 8 MPa with hydrogen gas and then reaction was conducted at 120° C. for 2 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 72.5%, a 1,5-pentanediol yield of 60.9% and a selectivity of 84.0%. Absolutely no 1,2-pentanediol by-product was detected.

Example 1-85

Synthesis of 1,5-pentanediol

After placing 103 mg of a solid obtained by the same method as Example 1-81 (Ir—Ru—Re/SiO$_2$ catalyst (6)) and 5.00 g (9.79 mmol) of a 20% tetrahydrofurfuryl alcohol water-soluble solution in the same apparatus as Example 1-76, the mixture was pressurized to 8 MPa with hydrogen gas and reaction was conducted at 120° C. for 9 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 97.8%, a 1,5-pentanediol yield of 71.6% and a selectivity of 73.2%. Absolutely no 1,2-pentanediol by-product was detected.

Example 1-86

Synthesis of 1,5-pentanediol

After placing 84.6 mg of a solid obtained by the same method as Example 1-81 (Ir—Ru—Re/SiO$_2$ catalyst (6)) and 5.00 g (2.45 mmol) of a 5% tetrahydrofurfuryl alcohol water-soluble solution in the same apparatus as Example 1-76, the mixture was pressurized to 1 MPa with hydrogen gas and then heated and stirred at 120° C. for 1 hour while stirring. After further adding 5.00 g (46.5 mmol) of a 95% tetrahydrofurfuryl alcohol water-soluble solution and pressurizing to 8 MPa with hydrogen gas, reaction was conducted at 120° C. for 20 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 80.3%, a 1,5-pentanediol yield of 65.3% and a selectivity of 81.3%. Absolutely no 1,2-pentanediol by-product was detected.

Example 1-87

Synthesis of 1,5-pentanediol

After placing 25 mg of the solid (Ir—Ru/SiO$_2$ catalyst (3)) obtained in Example 1-79, 5.00 g (2.45 mmol) of a 5% tetrahydrofurfuryl alcohol water-soluble solution and 0.92 mg (0.000743 mmol) of ammonium tetracosaoxoheptamolybdate(VI) in the same apparatus as Example 1-76, the mixture was pressurized to 8 MPa with hydrogen gas and then reacted at 120° C. for 18 hours while stirring. Mixture of the solid (Ir—Ru/SiO$_2$ catalyst (3)) and ammonium tetracosaoxoheptamolybdate(VI) and reduction treatment with hydrogen produced a hydrocracking catalyst (hereunder also referred to as "Ir—Ru—Mo/SiO$_2$ catalyst (1)"). Contacting this hydrocracking catalyst with tetrahydrofurfuryl alcohol in the presence of hydrogen gas promoted hydrocracking reaction. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 58.8%, a 1,5-pentanediol yield of 48.5% and a selectivity of 82.5%. Absolutely no 1,2-pentanediol by-product was detected.

Example 1-88

Production of Hydrocracking Catalyst

After impregnating 0.50 g of silica (SiO$_2$; product of Fuji Silysia Chemical, Ltd., trade name: CARiACT G-6) with a water-soluble solution comprising 0.244 g (0.104 mmol) of a dipotassium tetraoxoruthenate(VI) water-soluble solution (product of Furuya Metal Co., Ltd., ruthenium concentration: 4.3 mass %) added to 0.2 g of water, the mixture was dried at 110° C. for 7 hours. Next, a water-soluble solution of 34.7 mg (0.104 mmol) of iridium tetrachloride dissolved in 0.4 g of water was further impregnated into the silica and dried at 110° C. for 7 hours. After drying, a solution obtained by dissolving 27.9 mg (0.104 mmol) of ammonium tetraoxorhenate(VII) in 0.4 g of water was further impregnated therein and dried at 110° C. for 7 hours. The powder obtained in this manner was dried at 250° C. for 4 hours to obtain 575 mg of a solid comprising 4 mass % of iridium, 2.1 mass % of ruthenium and 3.9 mass % of rhenium supported on silica (hereunder also referred to as "Ir—Ru—Re/SiO$_2$ catalyst (7)").

Example 1-89

Synthesis of 1,5-pentanediol

After placing 25 mg of the solid obtained in Example 1-88 (Ir—Ru—Re/SiO$_2$ catalyst (7)), 5.00 g (2.45 mmol) of a 5% tetrahydrofurfuryl alcohol water-soluble solution and 20 mg of 1 mol/1 HCl in the same apparatus as Example 1-76, the mixture was pressurized to 8 MPa with hydrogen gas and reaction was conducted at 120° C. for 2 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 61.8%, a 1,5-pentanediol yield of 52.8% and a selectivity of 85.4%. Absolutely no 1,2-pentanediol by-product was detected.

Example 1-90

Production of Hydrocracking Catalyst

After impregnating 0.50 g of silica (SiO$_2$; product of Fuji Silysia Chemical, Ltd., trade name: CARiACT G-6) with a water-soluble solution obtained by combining 0.130 g (0.104 mmol) of a disodium tetraoxoruthenate(VI) water-soluble solution (product of Furuya Metal Co., Ltd., ruthenium concentration: 8.1 mass %) and 0.3 g of water, the mixture was dried at 110° C. for 7 hours. Next, a water-soluble solution obtained by dissolving 53.0 mg (0.104 mmol) of iridium hexachloride (product of Wako Pure Chemical Industries, Ltd., iridium concentration: 37.7 mass %) in 0.4 g of water was further impregnated into the silica and dried at 110° C. for 7 hours. After drying, it was further impregnated with a solution of 27.9 mg (0.104 mmol) of ammonium tetraoxorhenate (VII) dissolved in 0.4 g of water, and dried at 110° C. for 7 hours. The powder obtained in this manner was dried at 250° C. for 4 hours to obtain 575 mg of a solid comprising 4 mass % of iridium, 2.1 mass % of ruthenium and 3.9 mass % of rhenium supported on silica (hereunder also referred to as "Ir—Ru—Re/SiO$_2$ catalyst (8)").

Example 1-91

Synthesis of 1,5-pentanediol

After placing 25 mg of the solid obtained in Example 1-90 (Ir—Ru—Re/SiO$_2$ catalyst (8)), 5.00 g (2.45 mmol) of a 5% tetrahydrofurfuryl alcohol water-soluble solution and 40 mg of 1 mol/1 HCl in the same apparatus as Example 1-76, the mixture was pressurized to 8 MPa with hydrogen gas and reaction was conducted at 120° C. for 2 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 58.3%, a 1,5-pentanediol yield of 50.3% and a selectivity of 86.3%. Absolutely no 1,2-pentanediol by-product was detected.

Example 1-92

Production of Hydrocracking Catalyst

After impregnating 0.50 g silica (SiO$_2$; product of Fuji Silysia Chemical, Ltd., trade name: CARiACT G-6) with a water-soluble solution obtained by dissolving 53.0 mg (0.104 mmol) of iridium hexachloride (product of Wako Pure Chemical Industries, Ltd., iridium concentration: 37.7 mass %) in 0.4 g of water, it was dried at 110° C. for 7 hours. Next, the silica was impregnated with a water-soluble solution obtained by mixing 0.244 g (0.104 mmol) of a dipotassium tetraoxoruthenate(VI) water-soluble solution (product of Furuya Metal Co., Ltd., ruthenium concentration: 4.3 mass %) with 0.2 g of water, and dried at 110° C. for 7 hours. After drying, a solution obtained by dissolving 27.9 mg (0.104 mmol) of ammonium tetraoxorhenate(VII) in 0.4 g of water was further impregnated therein and dried at 110° C. for 7 hours. The powder obtained in this manner was dried at 250° C. for 4 hours to obtain 575 mg of a solid comprising 4 mass % of iridium, 2.1 mass % of ruthenium and 3.9 mass % of rhenium supported on silica (hereunder also referred to as "Ir—Ru—Re/SiO$_2$ catalyst (9)").

Example 1-93

Synthesis of 1,5-pentanediol

After placing 25 mg of the solid obtained in Example 1-92 (Ir—Ru—Re/SiO$_2$ catalyst (9)), 5.00 g (2.45 mmol) of a 5% tetrahydrofurfuryl alcohol water-soluble solution and 40 mg of 1 mol/1 HCl in the same apparatus as Example 1-76, the mixture was pressurized to 8 MPa with hydrogen gas and reaction was conducted at 120° C. for 2 hours while stirring. Upon completion of the reaction, the obtained reaction mixture was cooled to room temperature and filtered with an injector equipped with a membrane filter (0.45 μm).

The obtained filtrate was analyzed by gas chromatography, resulting in a tetrahydrofurfuryl alcohol conversion rate of 50.1%, a 1,5-pentanediol yield of 43.2% and a selectivity of 86.3%. Absolutely no 1,2-pentanediol by-product was detected.

Example 1-94

Production of Hydrocracking Catalyst Precursor

After impregnating 0.500 g of active carbon AC (product of Japan EnviroChemicals, Ltd., trade name: Shirasagi KL) with a ruthenium water-soluble solution comprising 236 mg (0.100 mmol) of a dipotassium tetraoxoruthenate(VI) water-soluble solution (product of Furuya Metal Co., Ltd., ruthenium concentration: 4.3 mass %) diluted with 1.50 g of water, it was dried at 110° C. for 4 hours. The obtained powder was impregnated with an iridium water-soluble solution comprising 241 mg (Ir: 0.102 mmol) of an iridium hexachloride water-soluble solution with an Ir concentration of 0.423 mmol/g diluted with 1.50 g of water, and then dried at 110° C. for 12 hours. After drying, it was fired at 250° C. for 4 hours to obtain 522 mg of a solid comprising 4 mass % of iridium and 2 mass % of ruthenium (hereunder also referred to as "Ir—Ru/AC") supported thereon.

Example 1-95 (Production of Hydrocracking Catalyst) and Example 1-96 (Synthesis of 1,5-pentanediol)

After placing 25.1 mg of the solid "Ir—Ru/AC" obtained in Example 1-94, 1.4 mg (0.0029 mmol) of dirhenium heptoxide and 2.0 g of water in an autoclave equipped with a 50 ml glass inner cylindrical tube, it was pressurized to 8 MPa with hydrogen gas and reaction was conducted at 120° C. for 2 hours while stirring. Following the reaction, the residue was filtered out by centrifugal separation and rinsed 3 times to obtain a hydrocracking catalyst (hereunder, "Ir—Ru—Re/AC catalyst (1)").

After then placing the previously obtained Ir—Ru—Re/AC catalyst (1) and 5.00 g (2.45 mmol) of a 5% tetrahydrofurfuryl alcohol water-soluble solution in an autoclave equipped with a 50 ml glass inner cylindrical tube, it was pressurized to 8 MPa with hydrogen gas and then reacted at 120° C. for 2 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 68.8%, a 1,5-pentanediol yield of 60.9% and a selectivity of 88.5%. Absolutely no 1,2-pentanediol by-product was detected.

Example 1-97 (Production of Hydrocracking Catalyst) and Example 1-98 (Synthesis of 1,5-pentanediol)

After placing 51.3 mg of the solid "Ir—Ru/AC" obtained in Example 1-94, 2.5 mg (0.0052 mmol) of dirhenium heptoxide and 4.0 g of water in an autoclave equipped with a 50 ml glass inner cylindrical tube, it was pressurized to 8 MPa with hydrogen gas and reaction was conducted at 120° C. for 2 hours while stirring. Following the reaction, the residue was filtered out by centrifugal separation and rinsed 3 times to obtain a hydrocracking catalyst (hereunder, "Ir—Ru—Re/AC catalyst (2)").

After then placing the obtained Ir—Ru—Re/AC catalyst (2) and 5.20 g (25.5 mmol) of a 50% tetrahydrofurfuryl alcohol water-soluble solution in an autoclave equipped with a 50 ml glass inner cylindrical tube, it was pressurized to 8 MPa with hydrogen gas and then reacted at 120° C. for 10 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 69.2%, a 1,5-pentanediol yield of 59.7% and a selectivity of 86.1%. Absolutely no 1,2-pentanediol by-product was detected.

Example 1-99 (Production of Hydrocracking Catalyst) and Example 1-100 (Synthesis of 1,5-pentanediol)

After placing 50.8 mg of the solid "Ir—Ru/AC" obtained in Example 1-94, 2.5 mg (0.0052 mmol) of dirhenium heptoxide and 4.0 g of water in an autoclave equipped with a 50 ml glass inner cylindrical tube, it was pressurized to 8 MPa with hydrogen gas and reaction was conducted at 120° C. for 2 hours while stirring. Following the reaction, the residue was filtered out by centrifugal separation and rinsed 3 times to obtain a hydrocracking catalyst (hereunder, "Ir—Ru—Re/AC catalyst (3)").

After then placing the obtained Ir—Ru—Re/AC catalyst (3) and 3.10 g (30.4 mmol) of tetrahydrofurfuryl alcohol water-soluble solution in an autoclave equipped with a 50 ml glass inner cylindrical tube, it was pressurized to 8 MPa with hydrogen gas and then reacted at 120° C. for 50 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 74.1%, a 1,5-pentanediol yield of 53.4% and a selectivity of 72.1%. Absolutely no 1,2-pentanediol by-product was detected.

These results indicated that a hydrocracking catalyst obtained by mixing:

(1) a metal compound (A) comprising any metal of Groups 3 to 11 of the Periodic Table, (2) ruthenium oxide compound (B1) and (3) a metal oxide (C) containing a metal of Group 5, Group 6 or Group 7 of the Periodic Table, and subjecting the mixture to reduction treatment, when contacted with an ether compound having a hydroxymethyl group in the presence of a hydrogen source, yields the corresponding hydroxy compound at a high reaction rate, at a high yield and in a highly selective manner.

The following starting materials (1) to (3) were then used to prepare and evaluate hydrocracking catalysts, as described below.

(1) Metal compound (A) including any metal of Groups 3 to 11 of the Periodic Table.

(2) High-valence metal compound (B2) including any metal of Groups 8 to 11 of the Periodic Table.

(3) Metal oxide (C) including any metal of Groups 5 to 7 of the Periodic Table.

Example 2-1

Production of Hydrocracking Catalyst

After adding 20.1 mg (0.060 mmol) of iridium trichloride.n hydrate (product of Ishizu Shiyaku, iridium concentration: 53 mass %), 20.6 mg (0.060 mmol) of disodium hexahydroxyplatinate(IV) and 5 ml of water to an autoclave equipped with a 50 ml glass inner cylindrical tube, the mixture was heated and stirred at 120° C. for 30 minutes to obtain a solution. The solution was temporarily cooled to room temperature, 17.4 mg (0.060 mmol) of potassium tetraoxorhenate(VII) was added, and the mixture was again heated and stirred at 120° C. for 30 minutes. It was then pressurized to 8 MPa at room temperature under a hydrogen atmosphere, and heated and stirred at 120° C. for 1 hour for reduction treatment of the mixture. The obtained solution was cooled to room temperature, the aqueous layer was removed by decantation and the hydrocracking catalyst (hereunder also referred to as "Ir—Pt—Re catalyst (1)") was obtained as a residue.

Example 2-2

Synthesis of 1,5-pentanediol

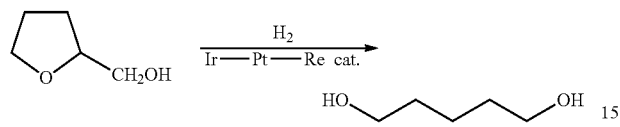

After placing the residue obtained in Example 2-1 (Ir—Pt—Re catalyst (1)) and 5.00 g (2.45 mmol) of a 5% tetrahydrofurfuryl alcohol water-soluble solution in the same apparatus as Example 2-1, the mixture was pressurized to 8 MPa with hydrogen gas and then reacted at 120° C. for 2 hours while stirring. This caused the chemical reaction represented above to proceed. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 100%, a 1,5-pentanediol yield of 44.6% and a selectivity of 44.6%. Absolutely no 1,2-pentanediol by-product was detected.

Example 2-3

Synthesis of 1,5-pentanediol

Reaction was carried out in the same manner as Example 2-2, except that the reaction temperature in Example 2-2 was changed from 120° C. to 100° C. As a result, the tetrahydrofurfuryl alcohol conversion rate was 96.1%, the 1,5-pentanediol yield was 81.8% and the selectivity was 85.2%. Absolutely no 1,2-pentanediol by-product was detected.

Comparative Example 2-1

Synthesis of 1,5-pentanediol

A hydrocracking catalyst was produced in the same manner as Example 2-1, except that the disodium hexahydroxyplatinate(IV) in Example 2-1 was not added, to prepare the hydrocracking catalyst: "Ir—Re catalyst".

Reaction was carried out in the same manner as Example 2-2, except that in Example 2-2, the reaction temperature during the reduction treatment was changed from 120° C. to 100° C. and the hydrogenation reaction catalyst was changed to the "Ir—Re catalyst" produced here. As a result, the tetrahydrofurfuryl alcohol conversion rate was 27.5%, the 1,5-pentanediol yield was 25.2% and the selectivity was 91.9%. Absolutely no 1,2-pentanediol by-product was detected.

Example 2-4

Synthesis of 1,5-pentanediol

Reaction was carried out in the same manner as Example 2-2, except that the reaction temperature in Example 2-2 was changed from 120° C. to 80° C. As a result, the tetrahydrofurfuryl alcohol conversion rate was 39.8%, the 1,5-pentanediol yield was 38.8% and the selectivity was 97.5%. Absolutely no 1,2-pentanediol by-product was detected.

Example 2-5

Production of Hydrocracking Catalyst

A hydrocracking catalyst (hereunder also referred to as "Ir—Pt—Re catalyst (2)") was obtained in the same manner as Example 2-1, except that in Example 2-1, the amount of potassium tetraoxorhenate(VII) was changed to 26.0 mg (0.090 mmol).

Example 2-6

Synthesis of 1,5-pentanediol

Reaction was carried out in the same manner as Example 2-2, except that in Example 2-2, the reaction temperature was changed from 120° C. to 80° C. and the hydrocracking catalyst was changed to the one produced in Example 2-5. As a result, the tetrahydrofurfuryl alcohol conversion rate was 73.3%, the 1,5-pentanediol yield was 69.8% and the selectivity was 95.2%. Absolutely no 1,2-pentanediol by-product was detected.

Example 2-7

Production of Hydrocracking Catalyst

A hydrocracking catalyst (hereunder also referred to as "Ir—Pt—Re catalyst (3)") was obtained in the same manner as Example 2-1, except that in Example 2-1, 17.9 mg (0.060 mmol) of hexahydroxyplatinic(IV) acid was used instead of disodium hexahydroxyplatinate(IV), and the amount of potassium tetraoxorhenate(VII) was changed to 26.0 mg (0.090 mmol).

Example 2-8

Synthesis of 1,5-pentanediol

Reaction was carried out in the same manner as Example 2-2, except that in Example 2-2, the reaction temperature was changed from 120° C. to 80° C. and the hydrocracking catalyst was changed to the one produced in Example 2-7. As a result, the tetrahydrofurfuryl alcohol conversion rate was 34.9%, the 1,5-pentanediol yield was 34.1% and the selectivity was 97.5%. Absolutely no 1,2-pentanediol by-product was detected.

Example 2-9

Production of Hydrocracking Catalyst

A hydrocracking catalyst (hereunder also referred to as "Ir—Pt—Mo catalyst (1)") was produced in the same manner as Example 2-1, except that in Example 2-1, 14.5 mg (0.060 mmol) of disodium tetraoxomolybdate dihydrate was used instead of potassium tetraoxorhenate(VII).

Example 2-10

Synthesis of 1,5-pentanediol

Reaction was carried out in the same manner as Example 2-2, except that in Example 2-2, the reaction temperature was changed from 120° C. to 100° C., the reaction time was changed from 1 hour to 10 hours, and the hydrocracking catalyst was the one produced in Example 2-9. As a result, the tetrahydrofurfuryl alcohol conversion rate was 62.2%, the 1,5-pentanediol yield was 57.1% and the selectivity was 91.9%. Absolutely no 1,2-pentanediol by-product was detected.

Example 2-11

Production of Hydrocracking Catalyst

A hydrocracking catalyst (hereunder also referred to as "Rh—Pt—Re catalyst (1)") was produced in the same manner as Example 2-1, except that in Example 2-1, 15.8 mg (0.060 mmol) of rhodium trichloride trihydrate was used instead of iridium trichloride.n hydrate.

Example 2-12

Synthesis of 1,5-pentanediol

Reaction was carried out in the same manner as Example 2-2, except that in Example 2-2, the reaction temperature was changed from 120° C. to 100° C. and the hydrocracking catalyst was changed to the one produced in Example 2-11. As a result, the tetrahydrofurfuryl alcohol conversion rate was 37.5%, the 1,5-pentanediol yield was 36.4% and the selectivity was 97.0%. Absolutely no 1,2-pentanediol by-product was detected.

Example 2-13

Synthesis of 1,5-pentanediol

Reaction was carried out in the same manner as Example 2-2, except that in Example 2-2, the reaction temperature was changed from 120° C. to 100° C., the reaction time was changed from 1 hour to 24 hours, and the hydrocracking catalyst was the one produced in Example 2-11. As a result, the tetrahydrofurfuryl alcohol conversion rate was 95.5%, the 1,5-pentanediol yield was 90.2% and the selectivity was 94.4%. Absolutely no 1,2-pentanediol by-product was detected.

Example 2-14

Production of Hydrocracking Catalyst

A hydrocracking catalyst (hereunder also referred to as "Ir—Au—Re catalyst (1)") was obtained in the same manner as Example 2-1, except that in Example 2-1, 14.9 mg (0.060 mmol) of trihydroxy gold(III) was used instead of disodium hexahydroxyplatinate(IV).

Example 2-15

Synthesis of 1,5-pentanediol

Reaction was carried out in the same manner as Example 2-2, except that in Example 2-2, the reaction temperature was changed from 120° C. to 100° C. and the hydrocracking catalyst was changed to the one produced in Example 2-14. As a result, the tetrahydrofurfuryl alcohol conversion rate was 44.4%, the 1,5-pentanediol yield was 39.9% and the selectivity was 89.7%. Absolutely no 1,2-pentanediol by-product was detected.

Example 2-16

Synthesis of 1,5-pentanediol

A hydrocracking catalyst (hereunder also referred to as "Ir—Rh—Re catalyst (1)") was obtained in the same manner as Example 2-1, except that in Example 2-1, 16.4 mg (0.060 mmol) of trisodium hexahydroxyrhodate(III) was used instead of disodium hexahydroxyplatinate(IV).

Example 2-17

Synthesis of 1,5-pentanediol

Reaction was carried out in the same manner as Example 2-2, except that in Example 2-2, the reaction temperature was changed from 120° C. to 100° C. and the hydrocracking catalyst was changed to the one produced in Example 2-16. As a result, the tetrahydrofurfuryl alcohol conversion rate was 41.3%, the 1,5-pentanediol yield was 38.6% and the selectivity was 93.5%. Absolutely no 1,2-pentanediol by-product was detected.

Example 2-18

Synthesis of 1,5-pentanediol

A hydrocracking catalyst (hereunder also referred to as "Rh—Rh—Re catalyst (1)") was obtained in the same manner as Example 2-1, except that in Example 2-1, 15.8 mg (0.060 mmol) of rhodium trichloride.trihydrate was used instead of iridium trichloride.n hydrate, and 16.4 mg (0.060 mmol) of trisodium hexahydroxyrhodate(III) was used instead of disodium hexahydroxyplatinate(IV).

Example 2-19

Synthesis of 1,5-pentanediol

Reaction was carried out in the same manner as Example 2-2, except that in Example 2-2, the reaction temperature was changed from 120° C. to 100° C. and the hydrocracking catalyst was changed to the one produced in Example 2-18. As a result, the tetrahydrofurfuryl alcohol conversion rate was 23.1%, the 1,5-pentanediol yield was 38.6% and the selectivity was 97.2%. Absolutely no 1,2-pentanediol by-product was detected.

Example 2-20

Synthesis of 1,5-pentanediol

A hydrocracking catalyst (hereunder also referred to as "Pt—Rh—Re catalyst (1)") was obtained in the same manner as Example 2-1, except that in Example 2-1, 16.0 mg (0.060 mmol) of platinum(II) chloride was used instead of iridium trichloride.n hydrate, and 16.4 mg (0.060 mmol) of trisodium hexahydroxyrhodate(III) was used instead of disodium hexahydroxyplatinate(IV).

Example 2-21

Synthesis of 1,5-pentanediol

Reaction was carried out in the same manner as Example 2-2, except that in Example 2-2, the reaction temperature was changed from 120° C. to 100° C. and the hydrocracking catalyst was changed to the one produced in Example 2-20. As a result, the tetrahydrofurfuryl alcohol conversion rate was 45.1%, the 1,5-pentanediol yield was 42.8% and the selectivity was 95.0%. Absolutely no 1,2-pentanediol by-product was detected.

Example 2-22

Synthesis of 1,5-pentanediol

Reaction was conducted in the same manner as Example 2-2, except that in Example 2-2, except that 3.03 g (29.7 mmol) of tetrahydrofurfuryl alcohol was used instead of the 5% tetrahydrofurfuryl alcohol water-soluble solution, the reaction temperature was changed from 120° C. to 100° C., the reaction time was changed from 1 hour to 24 hours, and the hydrocracking catalyst was changed to the one produced in Example 2-5. As a result, the tetrahydrofurfuryl alcohol conversion rate was 99.4%, the 1,5-pentanediol yield was 72.7% and the selectivity was 73.1%. Absolutely no 1,2-pentanediol by-product was detected.

Example 2-23 (Production of Hydrocracking Catalyst) and Example 2-24 (Synthesis of 1,5-pentanediol)

A platinum water-soluble solution was prepared by dissolving 30.3 mg (0.101 mmol) of hexahydroxyplatinic(IV) acid and 30.1 mg (0.298 mmol) of triethylamine in 1.20 g of water. This platinum water-soluble solution was impregnated into 0.500 g of silica ($SiO_2$; product of Fuji Silysia Chemical, Ltd., trade name: CARiACT G-6) and dried at 50° C. for 4 hours under reduced pressure with a vacuum pump. After impregnating the obtained powder with a rhodium water-soluble solution comprising 26.6 mg (0.101 mmol) of rhodium trichloride trihydrate dissolved in 1.20 g of water, it was dried at 110° C. for 12 hours. After drying, it was fired at 400° C. for 4 hours to obtain 515 mg of a solid comprising 2 mass % of rhodium and 4 mass % of platinum supported thereon (hereunder also referred to as "Rh—Pt/$SiO_2$").

After placing 50.6 mg of the solid "Rh—Pt/$SiO_2$" obtained in Example 2-23, 2.5 mg (0.0052 mmol) of dirhenium heptoxide and 5.00 g (2.45 mmol) of a 5% tetrahydrofurfuryl alcohol water-soluble solution in the same apparatus as Example 2-2, the mixture was pressurized to 8 MPa with hydrogen gas and then reacted at 120° C. for 2 hours while stirring. Mixture of the solid ("Rh—Pt/$SiO_2$") and dirhenium heptoxide and reduction treatment of the mixture with hydrogen produced a hydrocracking catalyst (hereunder also referred to as "Rh—Pt—Re/$SiO_2$ catalyst (1)"). Contacting this hydrocracking catalyst with tetrahydrofurfuryl alcohol in the presence of hydrogen gas promoted hydrocracking reaction.

The obtained filtrate was analyzed by gas chromatography, resulting in a tetrahydrofurfuryl alcohol conversion rate of 64.5%, a 1,5-pentanediol yield of 55.4% and a selectivity of 85.8%. Absolutely no 1,2-pentanediol by-product was detected.

Example 3-1

Production of Hydrocracking Catalyst

After adding 22.2 mg of iridium trichloride.n hydrate (product of Ishizu Shiyaku, iridium concentration: 53 mass %) (0.061 mmol of iridium), 19.6 mg (0.095 mmol) of potassium perruthenate(VII) and 5 ml of water into an autoclave equipped with a 50 ml glass inner cylindrical tube, the mixture was heated and stirred at 120° C. for 30 minutes. This was temporarily cooled to room temperature. To the cooled solution there was added 27.8 mg (0.095 mmol) of potassium tetraoxorhenate(VII) and 2.8 mg (0.047 mmol) of 1,2-diaminoethane, and the mixture was again heated and stirred at 120° C. for 30 minutes. It was then pressurized to 8 MPa at room temperature under a hydrogen atmosphere, and heated and stirred at 120° C. for 1 hour for reduction treatment of the mixture. The obtained solution was cooled to room temperature, the aqueous layer was removed by decantation and the hydrocracking catalyst (hereunder also referred to as "Ir—Ru—Re catalyst (11)") was obtained as a residue.

Example 3-2

Synthesis of 1,5-pentanediol

After placing the residue obtained in Example 3-1 (Ir—Ru—Re catalyst (11)) and 5.00 g (2.45 mmol) of a 5% tetrahydrofurfuryl alcohol water-soluble solution in the same apparatus as Example 3-1, the mixture was pressurized to 8 MPa with hydrogen gas and then reacted at 100° C. for 2 hours while stirring. Also, 1,2-diaminoethane was added during the course of the reaction. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 74.3%, a 1,5-pentanediol yield of 64.6% and a selectivity of 87.0%. Absolutely no 1,2-pentanediol by-product was detected.

Example 3-3

Production of Hydrocracking Catalyst

A water-soluble solution was prepared by dissolving 0.244 g of a dipotassium tetraoxoruthenate(VI) water-soluble solution (product of Furuya Metal Co., Ltd., ruthenium concentration: 4.3 mass %) (0.104 mmol of ruthenium) in 0.2 g of water. The water-soluble solution was impregnated into 0.50 g of silica ($SiO_2$, product of Fuji Silysia Chemical, Ltd., CARiACT G-6) and dried at 110° C. for 7 hours.

The impregnated and dried silica was impregnated with a water-soluble solution comprising 53.0 mg of iridium hexachloride (product of Wako Pure Chemical Industries, Ltd., iridium concentration: 37.7 mass %) (0.104 mmol of iridium) in 0.4 g of water. After drying at 110° C. for 7 hours, it was finally impregnated with a solution of 18.4 mg of ammonium tetracosaoxoheptamolybdate(VI) tetrahydrate (0.104 mmol of molybdenum) in 0.4 g of water, and dried at 110° C. for 7 hours to obtain a powder. The powder was dried at 250° C. for 4 hours to obtain 575 mg of a solid comprising 4 mass % of iridium, 2.1 mass % of ruthenium and 2.0 mass % of molybdenum supported on silica (hereunder also referred to as "Ir—Ru—Mo/$SiO_2$ catalyst (2)").

Example 3-4

Synthesis of 1,5-pentanediol

After then placing 25 mg of the Ir—Ru—Mo/$SiO_2$ catalyst (2) obtained in Example 3-3, 5.00 g (2.45 mmol) of a 5% tetrahydrofurfuryl alcohol water-soluble solution and 15.6 mg (0.0026 mmol) of a water-soluble solution containing 1 mass % 1,2-diaminoethane in an autoclave equipped with a 50 ml glass inner cylindrical tube, it was pressurized to 8 MPa with hydrogen gas and then reacted at 150° C. for 4 hours while stirring. Upon completion of the reaction, the obtained reaction mixture was cooled to room temperature and then filtered with an injector equipped with a membrane filter (0.45 μm).

The obtained filtrate was analyzed by gas chromatography, resulting in a tetrahydrofurfuryl alcohol conversion rate of 40.2%, a 1,5-pentanediol yield of 31.1% and a selectivity of 77.4%. Absolutely no 1,2-pentanediol by-product was detected.

These results indicated that a hydrocracking catalyst obtained by mixing:

(1) a metal compound (A) comprising any metal of Groups 3 to 11 of the Periodic Table, (2) a high-valence metal compound (B2) including any metal of Groups 8 to 11 of the Periodic Table, and (3) a metal oxide (C) containing a metal of Group 5, Group 6 or Group 7 of the Periodic Table, and subjecting the mixture to reduction treatment, when contacted with an ether compound having a hydroxymethyl group in the presence of a hydrogen source, yields the corresponding hydroxy compound at a high reaction rate, at a high yield and in a highly selective manner.

INDUSTRIAL APPLICABILITY

According to the invention it is possible to provide a hydrocracking catalyst that can accomplish hydrocracking of ether compounds with hydroxymethyl groups to produce the corresponding hydroxy compounds at a high reaction rate, at a high yield and in a highly selective manner. If the ether compounds are cyclic ethers, it is possible to produce the corresponding diol compounds. The obtained diol compounds are useful as, for example, polymer starting materials for polyesters, polycarbonates and polyurethanes, resin additives, pharmaceutical and agricultural intermediate starting materials, and various solvents.

The invention claimed is:

1. A method for producing a hydroxy compound, comprising a step of:
  contacting a hydrocracking catalyst with an ether compound having a hydroxymethyl group, in the presence of a hydrogen source; wherein
  the hydrocracking catalyst is obtainable by conducting a reduction treatment after mixing:
    a metal compound (A) including any one metal element selected from the group consisting of Ir, Rh, Ru, Pd, Pt, Au, La, Yb, Zr, Hf, Nb, Ta, Mo, W, Mn, Re, Co, Cu, and Ag,
    a compound (B) including at least one compound selected from the group consisting of a ruthenium oxide compound (B1) and a high-valence compound (B2) including any metal element selected from the group consisting of Pt, Au, and Rh, and
    a metal oxide (C) including any metal element selected from the group consisting of Re, Mo, and W; and
  the ether compound represented by general formula (1) is contacted with the hydrocracking catalyst in the presence of a hydrogen source, to obtain a hydroxy compound represented by general formula (2)

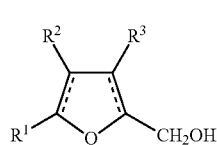

in the formula, $R^1$, $R^2$ and $R^3$ each independently represent hydrogen or a C1-5 alkyl group, and $R^1$ and $R^2$ or $R^2$ and $R^3$ bonded to adjacent carbons may optionally be bonded together to form a ring and a bond represented by the following formula (a) in the formula represents a single bond or a double bond;

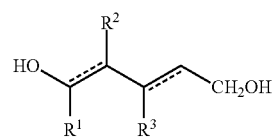

in the formula, $R^1$, $R^2$ and $R^3$ each independently represent hydrogen or a C1-5 alkyl group, and $R^1$ and $R^2$ or $R^2$ and $R^3$ bonded to adjacent carbons may optionally be bonded together to form a ring; and a bond represented by the following formula (a) in the formula represents a single bond or a double bond $$\text{-----}. \tag{a}$$

2. A method for producing a hydroxy compound, comprising a step of:
  contacting a hydrocracking catalyst with an ether compound having a hydroxymethyl group, in the presence of a hydrogen source; wherein
  the hydrocracking catalyst is obtainable by conducting a reduction treatment after mixing:
    a metal compound (A) including any one metal element selected from the group consisting of Ir, Rh, Ru, Pd, Pt, Au, La, Yb, Zr, Hf, Nb, Ta, Mo, W, Mn, Re, Co, Cu, and Ag,
    a compound (B) including at least one compound selected from the group consisting of a ruthenium oxide compound (B1) and a high-valence compound (B2) including any metal element selected from the group consisting of Pt, Au, and Rh, and
    a metal oxide (C) including any metal element selected from the group consisting of Re, Mo, and W; and
  the ether compound is at least one type of compound selected from the group consisting of compounds of general formulas (1a), (1b), (1c) and (1d);

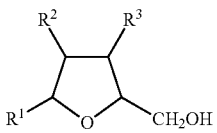

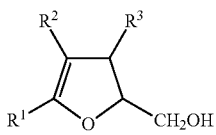
(1b)

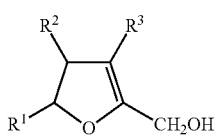
(1c)

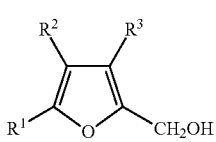
(1d)

in the formulas, $R^1$, $R^2$ and $R^3$ each independently represent hydrogen or a C1-5 alkyl group, and $R^1$ and $R^2$ or $R^2$ and $R^3$ bonded to adjacent carbons may optionally be bonded together to form a ring.

3. A method for producing a hydroxy compound, comprising a step of:

contacting a hydrocracking catalyst with an ether compound having a hydroxymethyl group, in the presence of a hydrogen source; wherein the hydrocracking catalyst is obtainable by conducting a reduction treatment after mixing:

a metal compound (A) including any one metal element selected from the group consisting of Ir, Rh, Ru, Pd, Pt, Au, La, Yb, Zr, Hf, Nb, Ta, Mo, W, Mn, Re, Co, Cu, and Ag, a compound (B) including at least one compound selected from the group consisting of a ruthenium oxide compound (B1) and a high-valence compound (B2) including any metal element selected from the group consisting of Pt, Au, and Rh, and a metal oxide (C) including any metal element selected from the group consisting of Re, Mo, and W; and the ether compound represented by general formula (3) is contacted with the hydrocracking catalyst in the presence of a hydrogen source, to obtain a hydroxy compound represented by general formula (4);

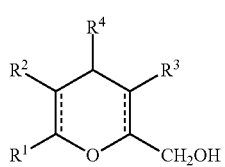
(3)

in the formula, $R^1$, $R^2$, $R^3$ and $R^4$ each independently represent hydrogen or a C1-5 alkyl group, and $R^1$, $R^2$, $R^3$ and $R^4$ bonded to adjacent carbons are optionally bonded together to form a ring; and a bond represented by the following formula (a) in the formula represents single a single bond or a double bond;

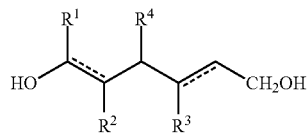
(4)

in the formula, $R^1$, $R^2$, $R^3$ and $R^4$ each independently represent hydrogen or a C1-5 alkyl group, and $R^1$, $R^2$, $R^3$ and $R^4$ bonded to adjacent carbons are optionally bonded together to form a ring; the bonds represented by the following formula (a) in the formula represents a single bond or a double bond $$----.\quad (a)$$

4. A method for producing a hydroxy compound, comprising a step of:

contacting a hydrocracking catalyst with an ether compound having a hydroxymethyl group, in the presence of a hydrogen source; wherein the hydrocracking catalyst is obtainable by conducting a reduction treatment after mixing:

a metal compound (A) including any one metal element selected from the group consisting of Ir, Rh, Ru, Pd, Pt, Au, La, Yb, Zr, Hf, Nb, Ta, Mo, W, Mn, Re, Co, Cu, and Ag, a compound (B) including at least one compound selected from the group consisting of a ruthenium oxide compound (B1) and a high-valence compound (B2) including any metal element selected from the group consisting of Pt, Au, and Rh, and a metal oxide (C) including any metal element selected from the group consisting of Re, Mo, and W; and the ether compound is at least one type of compound selected from the group consisting of compounds of general formulas (3a), (3b), (3c) and (3d);

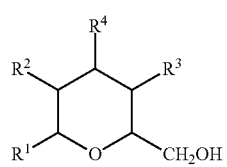
(3a)

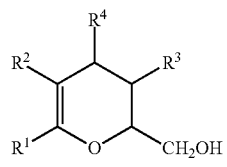
(3b)

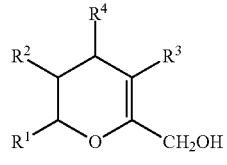
(3c)

-continued
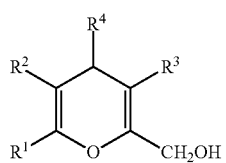
(3d)
in the formulas, $R^1$, $R^2$, $R^3$ and $R^4$ each independently represent hydrogen or a C1-5 alkyl group, and $R^1$, $R^2$, $R^3$ and $R^4$ bonded to adjacent carbons may optionally be bonded together to form a ring.
* * * * *